(12) United States Patent
Engelhardt et al.

(10) Patent No.: US 7,432,274 B2
(45) Date of Patent: *Oct. 7, 2008

(54) ACYCLIC NUCLEOSIDE DERIVATIVES

(75) Inventors: Per Engelhardt, Sotckholm (SE);
Marita Hogberg, Tullinge (SE);
Nils-Gunnar Johansson, Enhorna (SE);
Xiao-Xiong Zhou, Huddinge (SE);
Bjorn Lindborg, Bjornlunda (SE)

(73) Assignee: Medivir AB, Huddinge (SE)

( * ) Notice: Subject to any disclaimer, the term of this patent is extended or adjusted under 35 U.S.C. 154(b) by 766 days.

This patent is subject to a terminal disclaimer.

(21) Appl. No.: 10/741,615

(22) Filed: Dec. 19, 2003

(65) Prior Publication Data

US 2004/0132749 A1  Jul. 8, 2004

Related U.S. Application Data

(62) Division of application No. 10/076,833, filed on Feb. 14, 2002, now Pat. No. 6,703,394, which is a division of application No. 09/550,554, filed on Apr. 17, 2000, now Pat. No. 6,576,763, which is a division of application No. 09/146,194, filed on Sep. 3, 1998, now Pat. No. 6,255,312, which is a division of application No. 08/798,216, filed on Feb. 10, 1997, now Pat. No. 5,869,493.

(30) Foreign Application Priority Data

Feb. 16, 1996 (SE) .................................. 9600613
Feb. 16, 1996 (SE) .................................. 9600614

(51) Int. Cl.
*A61K 31/522* (2006.01)
*C07D 473/00* (2006.01)

(52) U.S. Cl. .............................. 514/263.38; 514/263.37; 544/276; 544/277

(58) Field of Classification Search ............ 514/263.38, 514/263.37; 544/276, 277
See application file for complete search history.

(56) References Cited

U.S. PATENT DOCUMENTS 5,216,141 A    6/1993  Benner (Continued)

FOREIGN PATENT DOCUMENTS

DE    19526163    2/1996

(Continued)

OTHER PUBLICATIONS

J.F. Nave et al., "Synthesis, Enzymatic Phosphorylation and Antiviral Activity of Acyclic Dienyl Phosphonate Derivatives of Guanine", Biorganic & Medical Chemistry Letters 6 179-184 (1996).

(Continued)

*Primary Examiner*—Shengjun Wang
(74) *Attorney, Agent, or Firm*—Birch Stewart Kolasch & Birch LLP

(57) ABSTRACT

Methods and novel intermediates for the preparation of and the treatment with acyclic nucleoside derivatives of the formula:

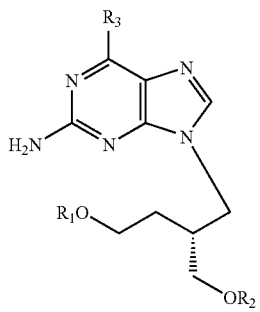

I where one of $R_1$ and $R_2$ is an amino acid acyl group and the other of $R_1$ and $R_2$ is a —C(O)$C_3$-$C_{21}$ saturated or monounsaturated, optionally substituted alkyl and $R_3$ is OH or H.

7 Claims, 2 Drawing Sheets

U.S. PATENT DOCUMENTS

| | | | |
|---|---|---|---|
| 5,216,142 A | 6/1993 | Horrobin et al. | |
| 5,284,837 A | 2/1994 | Lindborg et al. | |
| 5,473,063 A | 12/1995 | Classon et al. | |
| 5,543,414 A | 8/1996 | Nestor et al. | |
| 5,565,461 A | 10/1996 | Lindborg et al. | |
| 5,608,064 A | 3/1997 | Singh et al. | |
| 5,656,617 A | 8/1997 | Lindborg et al. | |
| 5,747,473 A | 5/1998 | Classon et al. | |
| 5,869,493 A | 2/1999 | Engelhardt et al. | |
| 6,255,312 B1 * | 7/2001 | Engelhardt et al. | 514/263.38 |
| 6,703,394 B2 * | 3/2004 | Engelhardt et al. | 514/263.38 |

FOREIGN PATENT DOCUMENTS

| | | |
|---|---|---|
| EP | 0099493 | 2/1984 |
| EP | 0186640 | 7/1986 |
| EP | 0308065 | 3/1989 |
| EP | 0165289 | 4/1989 |
| EP | 0343133 | 11/1989 |
| EP | 0375329 | 6/1990 |
| EP | 0654473 | 5/1995 |
| EP | 0694547 | 1/1996 |
| EP | 0728757 | 8/1996 |
| EP | 0827960 | 3/1998 |
| WO | 85/02845 | 7/1985 |
| WO | 89/03837 | 5/1989 |
| WO | 89/10923 | 11/1989 |
| WO | 93/07163 | 4/1993 |
| WO | 94/22887 | 10/1994 |
| WO | 94/24134 | 10/1994 |
| WO | 95/09855 | 4/1995 |
| WO | 95/22330 | 8/1995 |
| WO | 97/27194 | 7/1997 |
| WO | 97/27195 | 7/1997 |
| WO | 97/27196 | 7/1997 |
| WO | 97/27197 | 7/1997 |
| WO | 97/27198 | 7/1997 |
| WO | 97/30051 | 8/1997 |
| WO | 97/30052 | 8/1997 |

OTHER PUBLICATIONS

S. Halazy et al., "9-(Difluorophosphonalkyl) guanines as a New Class of Multisubstrate Analogue Inhibitors of Purine Nucleoside Phosphorylase", J. Am. Chem. Soc. vol. 113, pp. 315-317 (1991).
F. Vandendriessche et al., "Synthesis and Antiviral Activity of Acyclic Nucleosides with a 3(S), 5-Dihyroxypentyl or 4(R)-Methoxy-3(S), dihydroxypentyl Side Chain", J.Med.Chem. vol. 35, No. 8, pp. 1458-1465 (1992).
Benjamin et al., Pharmaceutical Research, 4, No. 2, 120-125 (1987).
Harden et al., J. Med. Chem. 32, 1738-1743 (1989).
Lake-Bakaar et al., Antimicrobial Agents and Chemotherapy, 33, No. 1, 110-112 (1989).
Hodge et al., Antimicrobial Agents and Chemotherapy, 33, No. 10., 1765-1773 (1989).
Terao et al., Chem. Pharm. Bull. 39(3), 823-825 (1991).
Ohsawa et al., Chem. Pharm. Bull. 41(11) 1906-1909 (1993).
Lowe, Antimicrobial Agents and Chemotherapy, 39, No. 8, 1802-1808 (1995).
Kim et al., Bioorganic & Medicinal Chemistry Letters 6, No. 15, 1849-1854 (1996).
M. Perez et al. "Stereocontrolled Synthesis of Phosphonate Derivatives of Tetrahydro-and Dihydro-2H-Pyranyl Nucleosides: The Selectivity of the Ferrier Rearrangement", Tetrahedron, vol. 6, No. 4, pp. 973-984 (1995).
G.R. Green, "The Effecet of the C-6 Constituent on the Regrioselectivity of N-Alkylation of 2-Aminopurines", Tetrahedron, vol. 46, No. 19, 99. 6903-6914 (1990).
M. Ashwell, "An Improved Route to Guanines Substituted at N-9", J. Chem. Soc., Chem, Commun., pp. 955-956 (1990).
"Drug Evaluation Manual," 1993 (A.M.A) p. 1723.
de Miranda, Antiviral Chem & Chemotherapy, 3(1), 1-8.
de Miranda, "Acyclovir Symposium" in Am. J. Medicine, vol. 73, p. 31.

* cited by examiner

ACYCLIC NUCLEOSIDE DERIVATIVES

This application is a Divisional of application Ser. No. 10/076,833, filed on Feb. 14, 2002, which is a Divisional of application Ser. No. 09/550,554, filed on Apr. 17, 2000, which is a Divisional of application Ser. No. 09/146,194, which was filed on Sep. 3, 1998, which is a Divisional of application Ser. No. 08/798,216, which was filed on Feb. 10, 1997 now U.S. Pat. No. 5,869,493, the entire contents of which are hereby incorporated by reference and for which priority is claimed under 35 U.S.C. § 120. This application also claims priority of Application Nos. 9600613-5 and 9600614-3, both filed in Sweden on Feb. 16, 1996 under 35 U.S.C. § 119.

TECHNICAL FIELD

This invention relates to the field of antivirals and in particular to derivatives of acyclic nucleosides useful against herpes and retroviral infections. The invention provides novel compounds, pharmaceutical compositions comprising these compounds, methods for the treatment or prophylaxis of viral infections employing them, methods for their manufacture and novel intermediates.

BACKGROUND TO THE INVENTION

The practical utility of many acyclic nucleosides is limited by their relatively modest pharmacokinetics. A number of prodrug approaches have been explored in an effort to improve the bioavailability of acyclic nucleosides in general. One of these approaches involves the preparation of ester derivatives, particularly aliphatic esters, of one or more of the hydroxy groups on the acyclic side chain.

European patent EP 165 289 describes the promising antiherpes agent 9-[4-hydroxy-(2-hydroxymethyl)butyl]guanine, otherwise known as H2G. European patent EP 186 640 discloses 6-deoxy H2G. European patent EP 343 133 discloses that these compounds, particularly the R-(−) enantiomer, are additionally active against retroviral infections such as HIV. Various derivatives of H2G, such as phosphonates, aliphatic esters (for example, the diacetate and the dipropionate) and ethers of the hydroxy groups on the acyclic side chain are disclosed in EP 343 133. This patent also discloses methods for the preparation of these derivatives comprising the condensation of the acyclic side chain to the N-9 position of a typically 6-halogenated purine moiety or, alternatively, the imidazole ring closure of a pyrimidine or furazano-[3,4-d]pyrimidine moiety or the pyrimidine ring closure of an imidazole moiety, where the acyclic side chain is already present in the precursor pyrimidine or imidazole moiety, respectively. In the broadest description of each of these methods the acyclic side chain is pre-derivatised but individual examples also show a one-step diacylation of H2G with acetic or proprionic anhydride and DMF.

Harnden, et al., J. Med. Chem. 32, 1738 (1989) investigated a number of short chain aliphatic esters of the acyclic nucleoside 9-[4-hydroxy-(3-hydroxymethyl)butyl] guanine, otherwise known as penciclovir, and its 6-deoxy analog. Famciclovir, a marketed antiviral agent, is the diacetyl derivative of 6-deoxy penciclovir.

Benjamin, et al., Pharm. Res. 4 No. 2, 120 (1987) discloses short chain aliphatic esters of 9-[(1,3-dihydroxy-2-propoxy)-methyl]guanine, otherwise known as ganciclovir. The dipropionate ester is disclosed to be the preferred ester.

Lake-Bakaar, et al., discloses in Antimicrob. Agents Chemother. 33 No. 1, 110-112 (1989) diacetate and dipropionate derivatives of H2G and monoacetate and diacetate derivatives of 6-deoxy H2G. The diacetate and dipropionate derivatives of H2G are reported to result in only modest improvements in bioavailability relative to H2G.

International patent application WO94/24134, published Oct. 27, 1994, discloses aliphatic ester prodrugs of the 6-deoxy N-7 analog of ganciclovir, including the di-pivaloyl, di-valeroyl, mono-valeroyl, mono-oleoyl and mono-stearoyl esters.

International patent application WO93/07163, published Apr. 15, 1993 and International patent application WO94/22887, published Oct. 13, 1994, both disclose mono-ester derivatives of nucleoside analogs derived from mono-unsaturated C18 or C20 fatty acids. U.S. Pat. No. 5,216,142, issued Jun. 1, 1993, also discloses long chain fatty acid mono-ester derivatives of nucleoside analogs.

A second approach to providing prodrugs of acyclic nucleosides involves the preparation of amino acid esters of one or more of the hydroxy groups on the acyclic side chain. European patent EP 99 493 discloses generally amino acid esters of acyclovir and European patent application EP 308 065, published Mar. 22, 1989, discloses the valine and isoleucine esters of acyclovir.

European patent application EP 375 329, published Jun. 27, 1990, discloses amino acid ester derivatives of ganciclovir, including the di-valine, di-isoleucine, di-glycine and di-alanine ester derivatives. International patent application WO95/09855, published Apr. 13, 1995, discloses amino acid ester derivatives of penciclovir, including the mono-valine and di-valine ester derivatives.

DE 19526163, published Feb. 1, 1996 and U.S. Pat. No. 5,543,414 issued Aug. 6, 1996, disclose achiral amino acid esters of ganciclovir.

European patent application EP 694 547, published Jan. 31, 1996, discloses the mono-L-valine ester of ganciclovir and its preparation from di-valyl-ganciclovir.

European patent application EP 654 473, published May 24, 1995, discloses various bis amino acid ester derivatives of 9-[1',2'-bishydroxymethyl)-cyclopropan-1'-yl]methylguanine.

International patent application WO95/22330, published Aug. 24, 1995, discloses aliphatic esters, amino acid esters and mixed acetate/valinate esters of the acyclic nucleoside 9-[3,3-dihydroxymethyl-4-hydroxy-but-1-yl]guanine. This reference discloses that bioavailability is reduced when one of the valine esters of the trivaline ester derivative is replaced with an acetate ester.

BRIEF DESCRIPTIONS OF THE INVENTION

We have found that diester derivatives of H2G bearing specific combinations of an amino acid ester and a fatty acid ester are able to provide significantly improved oral bioavailability relative to the parent compound (H2G). In accordance with a first aspect of the invention there is thus provided novel compounds of the formula I

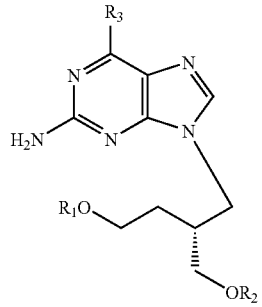

I where a) $R_1$ is —C(O)CH(CH(CH$_3$)$_2$)NH$_2$ or —C(O)CH(CH(CH$_3$)CH$_2$CH$_3$)NH$_2$ and $R_2$ is —C(O)C$_3$-C$_{21}$ saturated or monounsaturated, optionally substituted alkyl; or b) $R_1$ is —C(O)C$_3$-C$_{21}$ saturated or monounsaturated, optionally substituted alkyl and $R_2$ is —C(O)CH(CH(CH$_3$)$_2$)NH$_2$ or —C(O)CH(CH(CH$_3$)CH$_2$CH$_3$)NH$_2$; and $R_3$ is OH or H;

and pharmaceutically acceptable salts thereof.

The advantageous effect on oral bioavailability of the mixed fatty acid and amino acid esters of the invention is particularly unexpected in comparison to the oral bioavailability of the corresponding fatty acid esters. Based on the results using a urinary recovery assay (Table 1A) or a plasma drug assay (Table 1B) of H2G from rats, neither the mono or di-fatty acid esters of H2G provide any improvement in oral bioavailability relative to the parent compound H2G. Indeed the di-stearate derivative provided significantly lower bioavailability than the parent indicating that a stearate ester may be detrimental for improving oral bioavailability of H2G. Converting one or both of the hydroxyls in certain other acyclic nucleoside analogues to the corresponding valine or di-valine ester has been reported to improve bioavailability. Conversion of H2G to the coresponding mono- or di-valyl ester derivatives produced similar improvement in bioavailability relative to the parent compound. Given that fatty acid derivatives of H2G are shown to be detrimental for improving bioavailability, it was unexpected that a mixed amino acid/fatty acid diester derivative of H2G would provide improved or comparable oral bioavailability to that of the valine diester derivative of H2G, based on urine recovery and plasma drug assays, respectively.

TABLE 1A

| $R_1$ group | $R_2$ group | Bioavailability* |
|---|---|---|
| hydrogen | hydrogen | 8% |
| hydrogen | stearoyl | 12% |
| stearoyl | stearoyl | 1% |
| valyl | hydrogen | 29% |
| valyl | valyl | 36% |
| valyl | stearoyl | 56% |

*see Biological Example 1 below for details

TABLE 1B

| $R_1$ group | $R_2$ group | Bioavailability[#] |
|---|---|---|
| hydrogen | hydrogen | 3.8% |
| hydrogen | stearoyl | 1.9% |
| stearoyl | stearoyl | 0% |
| valyl | hydrogen | 31.3% |
| valyl | valyl | 35.0% |
| valyl | stearoyl | 29% |

[#]see Biological Example 2 below for details

The invention also provides pharmaceutical compositions comprising the compounds of Formula I and their pharmaceutically acceptable salts in conjunction with a pharmaceutically acceptable carrier or diluent. Further aspects of the invention include the compounds of Formula I and their pharmaceutically acceptable salts for use in therapy and the use of these compounds and salts in the preparation of a medicament for the treatment or prophylaxis of viral infection in humans or animals.

The compounds of the invention are potent antivirals, especially against herpes infections, such as those caused by *Varicella zoster* virus, Herpes simplex virus types 1 & 2, Epstein-Barr virus, Herpes type 6 (HHV-6) and type 8 (HHV-8). The compounds are particularly useful against Varicella zoster virus infections such as shingles in the elderly including post herpetic neuralgia or chicken pox in the young where the duration and severity of the disease can be reduced by several days. Epstein Barr virus infections amenable to treatment with the compounds include infectious mononucleosis/glandular fever which has previously not been treatable but which can cause many months of scholastic incapacity amongst adolescents.

The compounds of the invention are also active against certain retroviral infections, notably SIV, HIV-1 and HIV-2, and against infections where a transactivating virus is indicated.

Accordingly a further aspect of the invention provides a method for the prophylaxis or treatment of a viral infection in humans or animals comprising the administration of an effective amount of a compound of Formula I or its pharmaceutically acceptable salt to the human or animal.

Advantageously group $R_3$ is hydroxy or its tautomer=O so that the base portion of the compounds of the invention is the naturally occuring guanine, for instance in the event that the side chain is cleaved in vivo. Alternatively, $R_3$ may be hydrogen thus defining the generally more soluble 6-deoxy derivative which can be oxidised in vivo (e.g. by xanthine oxidase) to the guanine form.

The compound of formula I may be present in racemic form, that is a mixture of the 2R and 2S isomers. Preferably, however, the compound of formula I has at least 70%, preferably at least 90% R form, for example greater than 95%. Most preferably the compound of formula I is enantiomerically pure R form.

Preferably the amino acid of group $R_1$/$R_2$ is derived from an L-amino acid.

Preferably the fatty acid of group $R_1$/$R_2$ has in total an even number of carbon atoms, in particular, decanoyl ($C_{10}$), lauryl ($C_{12}$), myristoyl ($C_{14}$), palmitoyl ($C_{16}$), stearoyl ($C_{18}$) or eicosanoyl ($C_{20}$). Other useful $R_1$/$R_2$ groups include butyryl, hexanoyl, octanoyl or behenoyl ($C_{22}$). Further useful $R_1$/$R_2$ groups include those derived from myristoleic, myristelaidic, palmitoleic, palmitelaidic, n6-octadecenoic, oleic, elaidic, gandoic, erucic or brassidic acids. Monounsaturated fatty acid esters typically have the double bond in the trans configuration, preferably in the ω-6, ω-9 or ω-11 position, dependent upon their length. Preferably the $R_1/R_2$ group is derived from a fatty acid which comprises a $C_9$ to $C_{17}$ saturated, or n:9 monounsaturated, alkyl.

The saturated or unsaturated fatty acid or $R_1/R_2$ may optionally be substituted with up to five similar or different substituents independently selected from the group consisting of such as hydroxy, $C_1$-$C_6$ alkyl, $C_1$-$C_6$ alkoxy, $C_1$-$C_6$ alkoxy $C_1$-$C_6$ alkyl, $C_1$-$C_6$ alkanoyl, amino, halo, cyano, azido, oxo, mercapto and nitro, and the like.

Most preferred compounds of the formula I are those where $R_1$ is —C(O)CH(CH$_3$)$_2$)NH$_2$ or —C(O)CH(CH(CH$_3$)CH$_2$CH$_3$)NH$_2$ and $R_2$ is —C(O)C$_9$-C$_{17}$ saturated alkyl.

The term "lower alkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl gropus such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

The term "activated ester derivative" as used herein refers to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenyl derived esters and the like.

Preferred compounds of formula I include:
(R)-9-[2-(butyryloxymethyl)-4-(L-isoleucyloxy)butyl]guanine,
(R)-9-[2-(4-acetylbutyryloxymethyl)-4-(L-isoleucyloxy)butyl]guanine,
(R)-9-[2-(hexanoyloxymethyl)-4-(L-isoleucyloxy)butyl]guanine,
(R)-9-[4-(L-isoleucyloxy)-2-(octanoyloxymethyl)butyl]guanine,
(R)-9-[4-(L-isoleucyloxy)-2-(decanoyloxymethyl)butyl]guanine,
(R)-9-[4-(L-isoleucyloxy)-2-(dodecanoyloxymethyl)butyl]guanine,
(R)-9-[4-(L-isoleucyloxy)-2-(tetradecanoyloxymethyl)butyl]guanine,
(R)-9-[4-(L-isoleucyloxy)-2-(hexadecanoyloxymethyl)butyl]guanine,
(R)-9-[4-(L-isoleucyloxy)-2-(octadecanoyloxymethyl)butyl]guanine,
(R)-9-[2-(eicosanoyloxymethyl)-4-(L-isoleucyloxy)butyl]guanine,
(R)-9-[2-(docosanoyloxymethyl)-4-(L-isoleucyloxy)butyl]guanine,
(R)-9-[4-(L-isoleucyloxy)-2-((9-tetradecenoyl)oxymethyl)butyl]guanine,
(R)-9-[2-((9-hexadecenoyl)oxymethyl)-4-(L-isoleucyloxy)butyl]guanine,
(R)-9-[4-(L-isoleucyloxy)-2-((6-octadecenoyl)oxymethyl)butyl]guanine,
(R)-9-[4-(L-isoleucyloxy)-2-((9-octadecenoyl)oxymethyl)butyl]guanine,
(R)-9-[2-((11-eicosanoyl)-oxymethyl)-4-(L-isoleucyloxy)butyl]guanine,
(R)-9-[2-((13-docosenoyl)-oxymethyl)-4-(L-isoleucyloxy)butyl]guanine,
(R)-2-amino-9-[2-(butyryloxymethyl)-4-(L-isoleucyloxy)butyl]purine,
(R)-2-amino-9-[2-(4-acetylbutyryloxymethyl)-4-(L-isoleucyloxy)butyl]purine,
(R)-2-amino-9-[2-(hexanoyloxymethyl)-4-(L-isoleucyloxy)butyl]purine,
(R)-2-amino-9-[4-(L-isoleucyloxy)-2-(octanoyloxymethyl)butyl]purine,
(R)-2-amino-9-[4-(L-isoleucyloxy)-2-(decanoyloxymethyl)butyl]purine,
(R)-2-amino-9-[4-(L-isoleucyloxy)-2-(dodecanoyloxymethyl)butyl]purine,
(R)-2-amino-9-[4-(L-isoleucyloxy)-2-(tetradecanoyloxymethyl)butyl]purine,
(R)-2-amino-9-[4-(L-isoleucyloxy)-2-(hexadecanoyloxymethyl)butyl]purine,
(R)-2-amino-9-[4-(L-isoleucyloxy)-2-(octadecanoyloxymethyl)butyl]purine,
(R)-2-amino-9-[4-(L-isoleucyloxy)-2-(eicosanoyloxymethyl)butyl]purine,
(R)-2-amino-9-[2-(eicosanoyloxymethyl)-4-(L-isoleucyloxy)butyl]purine,
(R)-2-amino-9-[2-(docosanoyloxymethyl)-4-(L-isoleucyloxy)butyl]purine,
(R)-2-amino-9-[4-(L-isoleucyloxy)-2-((9-tetradecenoyl)oxymethyl)butyl]purine,
(R)-2-amino-9-[2-((9-hexadecenoyl)oxymethyl)-4-(L-isoleucyloxy)butyl]purine,
(R)-2-amino-9-[4-(L-isoleucyloxy)-2-((6-octadecenoyl)oxymethyl)butyl]purine,
(R)-2-amino-9-[4-(L-isoleucyloxy)-2-((9-octadecenoyl)oxymethyl)butyl]purine,
(R)-2-amino-9-[2-((11-eicosanoyl)oxymethyl)-4-(L-isoleucyloxy)butyl]purine, or (R)-2-amino-9-[2-((13-docosenoyl)oxymethyl)-4-(L-isoleucyloxy)butyl]purine, and their pharmaceutically accepable salts.

Further preferred compounds include:
(R)-9-[2-(butyryloxymethyl)-4-(L-valyloxy)butyl]guanine,
(R)-9-[2-(4-acetylbutyryloxymethyl)-4-(L-valyloxy)butyl]guanine,
(R)-9-[2-(hexanoyloxymethyl)-4-(L-valyloxy)butyl]guanine,
(R)-9-[2-(octanoyloxymethyl)-4-(L-valyloxy)butyl]guanine,
(R)-9-[2-(decanoyloxymethyl)-4-(L-valyloxy)butyl]guanine,
(R)-9-[2-(dodecanoyloxymethyl)-4-(L-valyloxy)butyl]guanine,
(R)-9-[2-(tetradecanoyloxymethyl-4-(L-valyloxy)butyl]guanine,
(R)-9-[2-hexadecanoyloxymethyl)-4-(L-valyloxy)butyl]guanine,
(R)-9-[2-(octadecanoyloxymethyl)-4-(L-valyloxy)butyl]guanine,
(R)-9-[2-(eicosanoyloxymethyl)-4-(L-valyloxy)butyl]guanine,
(R)-9-[2-(eicosanoyloxymethyl)-4-(L-valyloxy)butyl]guanine,
(R)-9-[2-(docosanoyloxymethyl)-4-(L-valyloxy)butyl]guanine,
(R)-9-[2-((9-tetradecenoyl)oxymethyl)-4-(L-valyloxy)butyl]guanine,
(R)-9-[2-((9-hexadecenoyl)oxymethyl)-4-(L-valyloxy)butyl]guanine,
(R)-9-[2-((6-octadecenoyl)oxymethyl)-4-(L-valyloxy)butyl]guanine,
(R)-9-[2-((9-octadecenoyl)oxymethyl)-4-(L-valyloxy)-butyl]guanine,
(R)-9-[2-((11-eicosanoyl)oxymethyl)-4-(L-valyloxy)butyl]guanine,
(R)-9-[2-((13-docosenoyl)oxymethyl)-4-(L-valyloxy)butyl]guanine,
(R)-2-amino-9-[2-(butyryloxymethyl)-4-(L-valyloxy)butyl]purine,
(R)-2-amino-9-[2-(4-acetylbutyryloxymethyl)-4-(L-valyloxy)butyl]purine,
(R)-2-amino-9-[2-(hexanoyloxymethyl)-4-(L-valyloxy)butyl]purine,
(R)-2-amino-9-[2-(octanoyloxymethyl)-4-(L-valyloxy)butyl]purine,
(R)-2-amino-9-[2-(decanoyloxymethyl)-4-(L-valyloxy)butyl]purine,
(R)-2-amino-9-[2-(dodecanoyloxymethyl)-4-(L-valyloxy)butyl]purine,
(R)-2-amino-9-[2-(tetradecanoyloxymethyl)-4-(L-valyloxy)butyl]purine,
(R)-2-amino-9-[2-(hexadecanoyloxymethyl)-4-(L-valyloxy)butyl]purine,
(R)-2-amino-9-[2-(octadecanoyloxymethyl)-4-(L-valyloxy)-butyl]purine,
(R)-2-amino-9-[2-(eicosanoyloxymethyl)-4-(L-valyloxy)butyl]purine,
(R)-2-amino-9-[2-(docosanoyloxymethyl)-4-(L-valyloxy)butyl]purine,
(R)-2-amino-9-[2-((9-tetradecenoyl)oxymethyl)-4-(L-valyloxy)butyl]purine,
(R)-2-amino-9-[2-((9-hexadecenoyl)oxymethyl)-4-(L-valyloxy)butyl]purine,
(R)-2-amino-9-[2-((6-octadecenoyl)oxymethyl)-4-(L-valyloxy)butyl]purine,
(R)-2-amino-9-[2-((9-octadecenoyl)oxymethyl)-4-(L-valyloxy)-butyl]purine,
(R)-2-amino-9-[2-((1-eicosenoyl)-oxymethyl)-4-(L-valyloxy)butyl]purine, or
(R)-2-amino-9-[2-((13-docosenoyl)-oxymethyl)-4-(L-valyloxy)butyl]purine;

and their pharmaceutically acceptable salts.

Other preferred compounds of formula I include:
(R)-9-[4-(butyryloxy)-2-(L-valyloxymethyl)butyl]guanine,
(R)-9-[4-(4-acetylbutyryloxy)-2-(L-valyloxymethyl)butyl]guanine,
(R)-9-[4-(hexanoyloxy)-2-(L-valyloxymethyl)butyl]guanine,
(R)-9-[4-(octanoyloxy)-2-(L-valyloxymethyl)butyl]guanine,
(R)-9-[4-(decanoyloxy)-2-(L-valyloxymethyl)butyl]guanine,
(R)-9-[4-(dodecanoyloxy)-2-(L-valyloxymethyl)butyl]guanine,
(R)-9-[4-(tetradecanoyloxy)-2-(L-valyloxymethyl)butyl]guanine,
(R)-9-[4-hexadecanoyloxy)-2-(L-valyloxymethyl)butyl]guanine,
(R)-9-[4-(octadecanoyloxy)-2-(L-valyloxymethyl)butyl]guanine,
(R)-9-[4-(eicosanoyloxy)-2-(L-valyloxymethyl)butyl]guanine,
(R)-9-[4-(docosanoyloxy)-2-(L-valyloxymethyl)butyl]guanine,
(R)-9-[4-((9-tetradecenoyl)oxy)-2-(L-valyloxymethyl)butyl]guanine,
(R)-9-[4-((9-hexadecenoyl)oxy)-2-(L-valyloxymethyl)butyl]guanine,
(R)-9-[4-((6-octadecenoyl)oxy)-2-(L-valyloxymethyl)butyl]guanine,
(R)-9-[4-((9-octadecenoyl)oxy)-2-(L-valyloxymethyl)-butyl]guanine,
(R)-9-[4-((11-eicosenoyl)oxy)-2-(L-valyloxymethyl)butyl]guanine,
(R)-9-[4-((13-docosenoyl)-oxy)-2-(L-valyloxymethyl)butyl]guanine,
(R)-2-amino-9-[4-(butyryloxy)-2-(L-valyloxymethyl)butyl]purine,
(R)-2-amino-9-[4-(4-acetylbutyryloxy)-2-(L-valyloxymethyl)butyl]purine,
(R)-2-amino-9-[4-(hexanoyloxy)-2-(L-valyloxymethyl)butyl]purine,
(R)-2-amino-9-[4-(octanoyloxy)-2-(L-valyloxymethyl)butyl]purine,
(R)-2-amino-9-[4-(decanoyloxy)-2-(L-valyloxymethyl)butyl]purine,
(R)-2-amino-9-[4-(dodecanoyloxy)-2-(L-valyloxymethyl)butyl]purine,
(R)-2-amino-9-[4-(tetradecanoyloxy)-2-(L-valyloxymethyl)butyl]purine,
(R)-2-amino-9-[4-(hexadecanoyloxy)-2-(L-valyloxymethyl)butyl]purine,
(R)-2-amino-9-[4-(octadecanoyloxy)-2-(L-valyloxymethyl)-butyl]purine,
(R)-2-amino-9-[4-(eicosanoyloxy)-2-(L-valyloxymethyl)butyl]purine,
(R)-2-amino-9-[4-(docosanoyloxy)-2-(L-valyloxymethyl)butyl]purine, (R)-2-amino-9-[4-((9-tetradecenoyl)oxy)-2-(L-valyloxymethyl)butyl]purine,
(R)-2-amino-9-[4-((9-hexadecenoyl)oxy)-2-(L-valyloxymethyl)butyl]purine,
(R)-2-amino-9-[4-((6-octadecenoyl)oxy)-2-(L-valyloxymethyl)butyl]purine,
(R)-2-amino-9-[4-((9-octadecenoyl)oxy)-2-(L-valyloxymethyl)butyl]purine,
(R)-2-amino-9-[4-((11-eicosenoyl)oxy)-2-(L-valyloxy)butyl]purine,
(R)-2-amino-9-[2-((13-docosenoyl)oxymethyl)-2-(L-valyloxy)butyl]purine, or and their pharmaceutically acceptable salts.

The compounds of formula I can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Hydrochloric acid salts are convenient.

The compounds of Formula I may be isolated as the hydrate. The compounds of the invention may be isolated in crystal form, preferably homogenous crystals, and thus an additional aspect of the invention provides the compounds of Formula I in substantially pure crystalline form, comprising >70%, preferably >90% homogeneous crystalline material for example >95% homogeneous crystalline material.

The compounds of the invention are particularly suited to oral administration, but may also be administered rectally, vaginally, nasally, topically, transdermally or parenterally, for instance intramuscularly, intravenously or epidurally. The compounds may be administered alone, for instance in a capsule, but will generally be administered in conjunction with a pharmaceutically acceptable carrier or diluent. The invention extends to methods for preparing a pharmaceutical composition comprising bringing a compound of Formula I or its pharmaceutically acceptable salt in conjunction or association with a pharmaceutically acceptable carrier or vehicle.

Oral formulations are conveniently prepared in unit dosage form, such as capsules or tablets, employing conventional carriers or binders such as magnesium stearate, chalk, starch, lactose, wax, gum or gelatin. Liposomes or synthetic or natural polymers such as HPMC or PVP may be used to afford a sustained release formulation. Alternatively the formulation may be presented as a nasal or eye drop, syrup, gel or cream comprising a solution, suspension, emulsion, oil-in-water or water-in-oil preparation in conventional vehicles such as water, saline, ethanol, vegetable oil or glycerine, optionally with flavourant and/or preservative and/or emulsifier.

The compounds of the invention may be administered at a daily dose generally in the range 0.1 to 200 mg/kg/day, advantageously, 0.5 to 100 mg/kg/day, more preferably 10 to 50 mg/kg/day, such as 10 to 25 mg/kg/day. A typical dosage rate for a normal adult will be around 50 to 500 mg, for example 300 mg, once or twice per day for herpes infections and 2 to 10 times this dosage for HIV infections.

As is prudent in antiviral therapy, the compounds of the invention can be administered in combination with other antiviral agents, such as acyclovir, valcyclovir, penciclovir, famciclovir, ganciclovir and its prodrugs, cidofovir, foscarnet and the like for herpes indications and AZT, ddI, ddC, d4T, 3TC, foscarnet, ritonavir, indinavir, saquinavir, delaviridine, Vertex VX 478, Agouron AG1343 and the like for retroviral indications.

The compounds of the invention can be prepared de novo or by esterification of the H2G parent compound which is prepared, for example, by the synthesis methodology disclosed in European Patent EP 343 133, which is incorporated herein by reference.

A typical reaction scheme for the preparation of H2G is depicted overleaf:

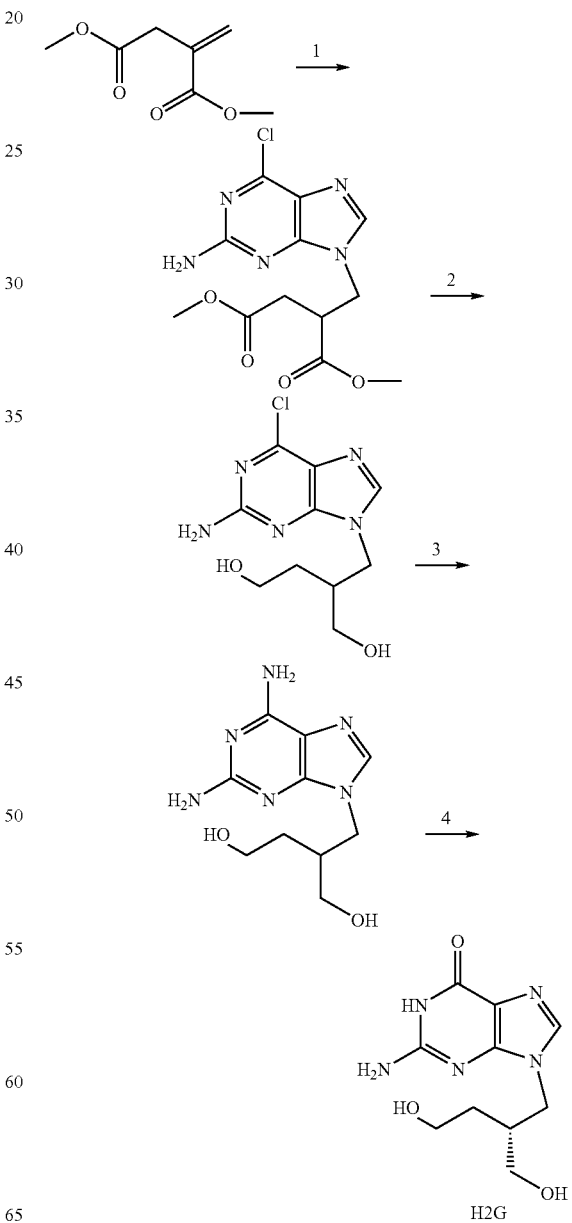

The condensation in step 1 is typically carried out with a base catalyst such as NaOH or $Na_2CO_3$ in a solvent such as DMF. Step 2 involves a reduction which can be performed with $LiBH_4$/tetrahydrofuran in a solvent such as t-BuOH. The substitution in step 3 of the chlorine with an amino group can be performed under pressure with ammonia. Step 4 employs adenosine deaminase which can be conveniently immobilized on a solid support. Cooling the reaction mixture allows unreacted isomeric precursor to remain in solution thereby enhancing purity.

Starting materials for compounds of the invention in which $R_3$ is hydrogen may be prepared as shown in European Patent EP 186 640, the contents of which are incorporated herein by reference. These starting materials may be acylated as described for H2G below, optionally after protecting the purine 2-amino group with a conventional N-protecting group as defined above, especially BOC (t-BuO—CO—), Z (BnO—CO—) or $Ph_3C$—.

The compounds of the invention may be prepared from H2G as described below in Schemes A and B.

A. Direct Acylation Method

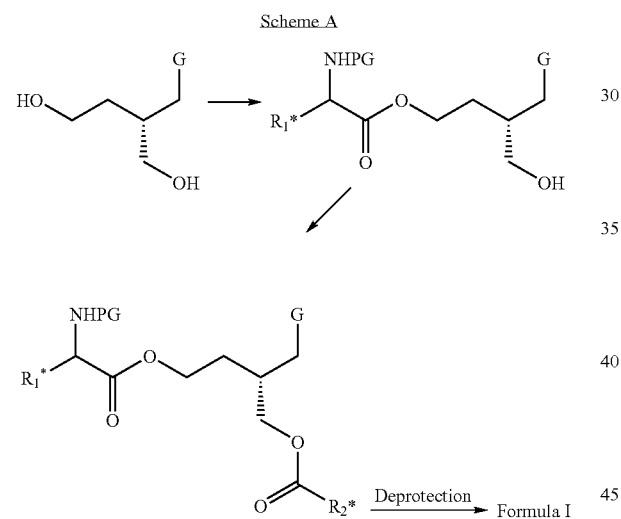

Scheme A

Scheme A depicts the preparation of compounds in which $R_1$ is derived from the amino acid and $R_2$ is derived from the fatty acid, but the converse scheme is applicable to compounds where $R_1$ is derived from the fatty acid and $R_2$ is derived from the amino acid ester. In the variant specifically depicted in scheme A above, G is guanine or 6-deoxyguanine, PG is an optional N-protecting group or hydrogen, $R_1^*$ is the valine or isoleucine side chain and $R_2^*$ is the fatty acid chain. H2G is depicted above as a starting material but this of course may be optionally protected at $R_3$ or the 2 position of the purine with conventional N-protecting groups (not shown). The H2G (derivative) reacts in the first step with an activated $R_1$ α-amino acid derivative, as further described below, in a solvent such as dimethylformamide or pyridine, to give a monoacylated product. The $R_1$ α-amino acid may be suitably N-protected with N-BOC or N-CBz or the like. Under controlled conditions, the first acylation can be made to predominantly take place at the side chain 4-hydroxy group on the side chain of H2G. These controlled conditions can be achieved, for example, by manipulating the reagent concentrations or rate of addition, especially of the acylating agent, by lowering the temperature or by the choice of solvent. The reaction can be followed by TLC to monitor the controlled conditions.

After purification, the $R_1$ monoacylated compounds are further acylated on the side chain 2-$CH_2OH$ group with the appropriate activated fatty acid derivative to give diacylated products using similar procedures as for the first esterification step. The diester products are subsequently subjected to a conventional deprotection treatment using for example trifluoroacetic acid, HCl(aq)/dioxane or hydrogenation in the presence of catalyst to give the desired compound of Formula I. The compound may be in salt form depending on the deprotection conditions.

The activated $R_1/R_2$ acid derivative used in the various acylations may comprise e.g. the acid halide, acid anhydride, activated acid ester or the acid in the presence of coupling reagent, for example dicyclohexylcarbodiimide, where "acid" in each case represents the corresponding $R_1/R_2$ amino acid or the $R_1/R_2$ fatty acid. Representative activated acid derivatives include the acid chloride, formic and acetic acid derived mixed anhydrides, anhydrides derived from alkoxycarbonyl halides such as isobutyloxycarbonylchloride and the like, N-hydroxysuccinamide derived esters, N-hydroxyphthalimide derived esters, N-hydroxy-5-norbornene-2,3-dicarboxamide derived esters, 2,4,5-trichlorophenol derived esters and the like.

B. Via Protection of the Side Chain 4-Hydroxy Group:

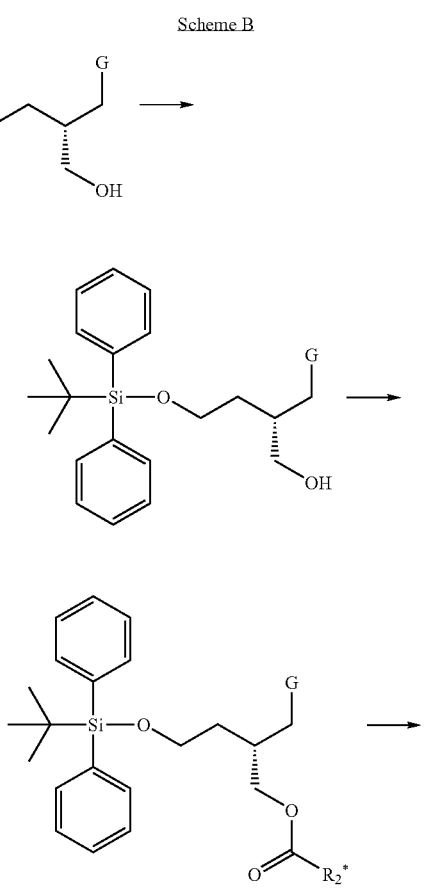

Scheme B

-continued

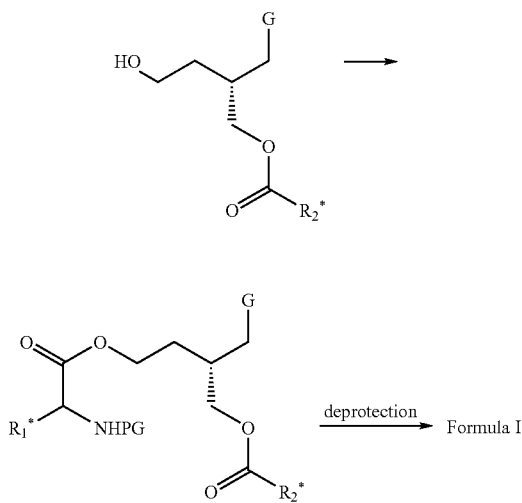

wherein G, PG, $R_1^*$ and $R_2^*$ are as described for scheme A.

Scheme B has been exemplified with reference to the preparation of a compound where $R_1$ is derived from an amino acid and $R_2$ is derived from the fatty acid ester, but a converse scheme will be applicable to compounds where $R_2$ is derived from the amino acid and $R_1$ is derived from the fatty acid. This scheme relies on regioselective protection of the H2G side chain 4-hydroxy group with a bulky protecting group. In scheme B above this is depicted as t-butyldiphenyl-silyl, but other regioselective protecting groups such as trityl, 9-(9-phenyl)xanthenyl, 1,1-bis(4-methylphenyl)-1'-pyrenyl-methyl may also be appropriate. The resulting product is acylated at the side chain 2-hydroxymethyl group using analogous reagents and procedures as described in scheme A above, but wherein the activated acid derivative is the $R_2$ fatty acid, for example, myristic, stearic, oleic, elaidic acid chloride and the like. The thus monoacylated compounds are subjected to appropriate deprotection treatment to remove the side chain 4-hydroxy protecting group which can be done in a highly selective manner with such reagents, depending on the regioselective protecting group, as HF/pyridine and the like and manipulation of the reaction conditions, viz reagent concentration, speed of addition, temperature and solvent etc, as elaborated above. The then free side chain 4-hydroxy group is acylated with the activated α-amino acid in a similar way as described in scheme A above.

Additional techniques for introducing the amino acid ester of $R_1/R_2$, for instance in schemes A, B, C or D herein include the 2-oxa-4-aza-cycloalkane-1,3-dione method described in international patent application no. WO 94/29311.

Additional techniques for introducing the fatty acid ester of $R_1/R_2$, for instance in schemes A, B, C or D herein include the enzymatic route described in Preparative Biotransformations 1.11.8 (Ed S M Roberts, J Wiley and Son, NY, 1995) with a lipase such as SP 435 immobilized Candida antarcticus (Novo Nordisk), porcine pancreatic lipase or Candida rugosa lipase. Enzymatic acylation is especially convenient where it is desired to avoid N-protection and deprotection steps on the other acyl group or the purine 2-amine.

An alternative route to compounds of Formula I in which $R_3$ is hydrogen is to 6-activate the correponding guanine compound of Formula I (wherein the amino acid ester moiety of $R_1/R_2$ is optionally protected with conventional N-protecting groups such as BOC) with an activating group such as halo. The thus activated 6-purine is subsequently reduced to purine, for instance with a palladium catalyst and deprotected to the desired 6-deoxy H2G di-ester.

A further aspect of the invention thus provides a method for the preparation of the compounds of formula I comprising
a) optionally N-protecting the purine 2 and/or 6 positions of a compound of formula I wherein $R_1$ and $R_2$ are each hydrogen;
b) regioselectively acylating the compound of Formula 1 at the side chain 4-hydroxy group with either
  i) an optionally N-protected valine or isoleucine group,
  ii) an optionally substituted, saturated or monounsaturated $C_3$-$C_{21}$COOH derivative, or
  iii) a regioselective protecting group;
c) acylating at the side chain 2-hydroxymethyl group with
  i) an optionally N-protected valine or isoleucine derivative, or
  ii) an optionally substituted, saturated or monounsaturated $C_3$-$C_{21}$COOH derivative;
d) replacing the regioselective protecting group at R1, if present, with
  i) an optionally N-protected valine or isoleucine derivative; or
  ii) an optionally substituted, saturated or monounsaturated $C_3$-$C_{21}$COOH derivative; and
e) deprotecting the resulting compound as necessary.

Schemes A and B above employ selective acylation to stepwise add the amino acid and fatty acid esters. An alternative process for the preparation of the compounds of formula I starts with a diacylated H2G derivative, wherein both the acyl groups are the same, and employs selective removal of one of the acyl groups to obtain a monoacyl intermediate which is then acylated with the second, differing, acyl group in the same manner as Schemes A and B above.

Accordingly a further aspect of the invention provides a method for the preparation of a compound of the formula I, as defined above, which method comprises
A) the monodeacylation of a diacylated compound corresponding to formula I wherein $R_1$ and $R_2$ are both a valyl or isoleucyl ester (which is optionally N-protected) or are $R_1$ and $R_2$ are both —C(=O)$C_3$-$C_{21}$ saturated or monounsaturated, optionally substituted alkyl; and
B) acylating the thus liberated side chain 4-hydroxy or side chain 2-hydroxymethyl group with the corresponding valyl, isoleucyl or —C(=O)$C_3$-$C_{21}$ saturated or monounsaturated, optionally substituted alkyl; and
C) deprotecting as necessary.

This alternative process has the advantage that the preparation of the diacylated H2G derivative is facile and requires little or no purification steps. Selective removal of one only of the acyl groups of a diacylated H2G derivative can be achieved by manipulating the reaction conditions, in particular the temperature, rate of reactant addition and choice of base.

Compounds amenable to this alternative synthesis route are thus of the formula:

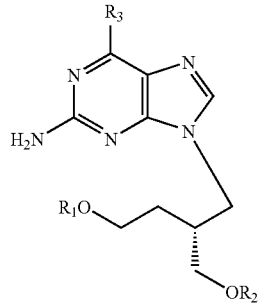

where $R_1$ and $R_2$ are valyl or isoleucyl (which are optionally N-protected) or a —C(=O)$C_3$—$C_{21}$ saturated or monounsaturated, optionally substituted alkyl; and $R_3$ is OH or H.

For ease of synthesis in this alternative route, it is preferred that $R_1$ and $R_2$ are both initially identical and are most preferably the same amino acid ester. Such a di-amino acid ester will generally be N-protected during its preparation and may be used directly in this condition in the selective deacylation step. Alternatively, such an N-protected di-aminoacylated H2G derivative may be deprotected and optionally reprotected, as described below. The unprotected di-aminoacyl H2G derivative thus comprises one of the following compounds:

(R)-9-[2-(L-isoleucyloxymethyl)-4-(L-isoleucyloxy)butyl] guanine,
(R)-9-[2-(L-valyloxymethyl)-4-(L-valyloxy)butyl]guanine,
(R)-2-amino-9-[4-(L-isoleucyloxy)-2-(L-isoleucyloxymethyl)butyl]purine, and
(R)-2-amino-9-[4-(L-valyloxy)-2-(L-valyloxymethyl)butyl] purine.

These unprotected H2G diacylated derivatives can be directly subject to selective deacylation of one of the acyl groups (typically the side chain 4-position acyl) followed by enzymatic acylation of the liberated 4-hydroxy as described above. Alternatively, the unprotected H2G diacylated derivative can be re-protected and then subjected to the selective deacylation, followed in turn by conventional acylation with the fatty acid ester, as described in Schemes A and B. Conveniently, such a reprotection step is done with a different N-protecting group, having properties appropriate to the subsequent acylation. For example, it is convenient to employ a lipophilic N-protecting group, such as Fmoc when preparing a di-amino acid H2G derivative, as the lipophilic nature of the protecting group assists with separation of the acylated products. On the other hand, the lipophilic nature of Fmoc is of less utility when conducting an acylation with a fatty acid, and thus it is convenient to reprotect a diacylated H2G with an alternative N-protecting group such as BOC.

It will also be apparent that the preparation of the compounds of formula I can commence with the novel monoacylated intermediates of step b i), ii) or iii) in the above defined first method aspect of the invention. These compounds are thus of the formula:

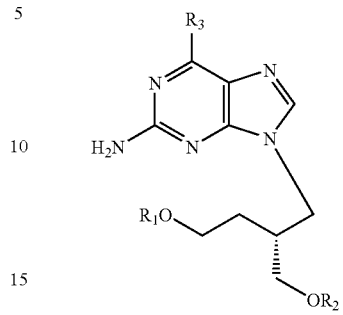

where one of $R_1$ and $R_2$ is
i) —C(O)CH(CH($CH_3$)$_2$)$NH_2$ or —C(O)CH(CH($CH_3$)$CH_2CH_3$)$NH_2$
ii) a —C(=O)$C_3$-$C_{21}$ saturated or monounsaturated, optionally substituted alkyl, or
iii) a regioselective protecting group;
the other of $R_1$ and $R_2$ is hydrogen; and
$R_3$ is OH or H;
Useful compounds thus include:
(R)-9-[2-hydroxymethyl-4-(t-butyldiphenylsilyl)butyl]guanine,
(R)-9-[2-hydroxymethyl-4-(trityloxy)butyl]guanine,
(R)-9-[2-hydroxymethyl-4-(9-(9-phenyl)xanthenyloxy)butyl]guanine,
(R)-9-[2-hydroxymethyl-4-(1,1-bis(4-methylphenyl)-1'-pyrenylmethyloxy)butyl]guanine,
(R)-9-[2-hydroxymethyl-4-(decanoyloxy)butyl]guanine,
(R)-9-[2-hydroxymethyl)-4-(dodecanoyloxy)butyl]guanine,
(R)-9-[2-hydroxymethyl-4-(tetradecanoyloxy)butyl]guanine,
(R)-9-[2-hydroxymethyl)-4-(hexadecanoyloxy)butyl]guanine,
(R)-9-[2-hydroxymethyl-4-(octadecanoyloxy)butyl]guanine,
(R)-9-[2-hydroxymethyl)-4-(eicosanoyloxy)butyl]guanine,
(R)-9-[2-hydroxymethyl-4-(docosanoyloxy)butyl]guanine,
(R)-9-[4-hydroxy-2-(decanoyloxymethyl)butyl]guanine,
(R)-9-[4-hydroxy-2-(dodecanoyloxymethyl) butyl]guanine,
(R)-9-[4-hydroxy-2-(tetradecanoyloxymethyl)butyl]guanine,
(R)-9-[4-hydroxy-2-(hexadecanoyloxymethyl)butyl]guanine,
(R)-9-[4-hydroxy-2-(octadecanoyloxymethyl)butyl]guanine,
(R)-9-[4-hydroxy-2-(eicosanoyloxymethyl)butyl]guanine,
(R)-9-[4-hydroxy-2-(docosanoyloxymethyl)butyl]guanine,
(R)-9-[2-hydroxymethyl-4-(L-valyloxy)butyl]guanine,
(R)-9-[2-hydroxymethyl)-4-(L-isoleucyloxy)butyl]guanine,
(R)-9-[4-hydroxy-2-(L-isoleucyloxymethyl)butyl]guanine,
(R)-9-[4-hydroxy-2-(L-valyloxymethyl) butyl]guanine.
(R)-2-amino-9-[2-hydroxymethyl-4-(L-valyloxy)butyl]purine,
(R)-2-amino-9-[2-hydroxymethyl)-4-(L-isoleucyloxy)butyl] purine,
(R)-2-amino-9-[4-hydroxy-2-(L-isoleucyloxymethyl)butyl] purine, and (R)-2-amino-9-[4-hydroxy-2-(L-valyloxymethyl)butyl]purine.

Regioselectively protected, sidechain 4-hydroxy intermediates from step c) of the above described first method aspect of the invention are also novel compounds. Useful compounds thus include:

(R)-9-[2-decanoyloxymethyl-4-(t-butyldiphenylsilyl)butyl]guanine,
(R)-9-[2-dodecanoyloxymethyl-4-(t-butyldiphenylsilyl)butyl]guanine,
(R)-9-[2-tetradecanoyloxymethyl-4-(t-butyldiphenylsilyl)butyl]guanine,
(R)-9-[2-hexadecanoyloxymethyl-4-(t-butyldiphenylchlorosilane)butyl]guanine,
(R)-9-[2-octadecanoyloxymethyl-4-(t-butyldiphenylsilyl)butyl]guanine,
(R)-9-[2-eicosanoyloxymethyl-4-(t-butyldiphenylsilyl)butyl]guanine,
(R)-9-[2-docosanoyloxymethyl-4-(t-butyldiphenylsilyl)butyl]guanine, An alternative process for the preparation of compounds of the invention of the formula I wherein $R_3$ is —OH is shown in Scheme C.

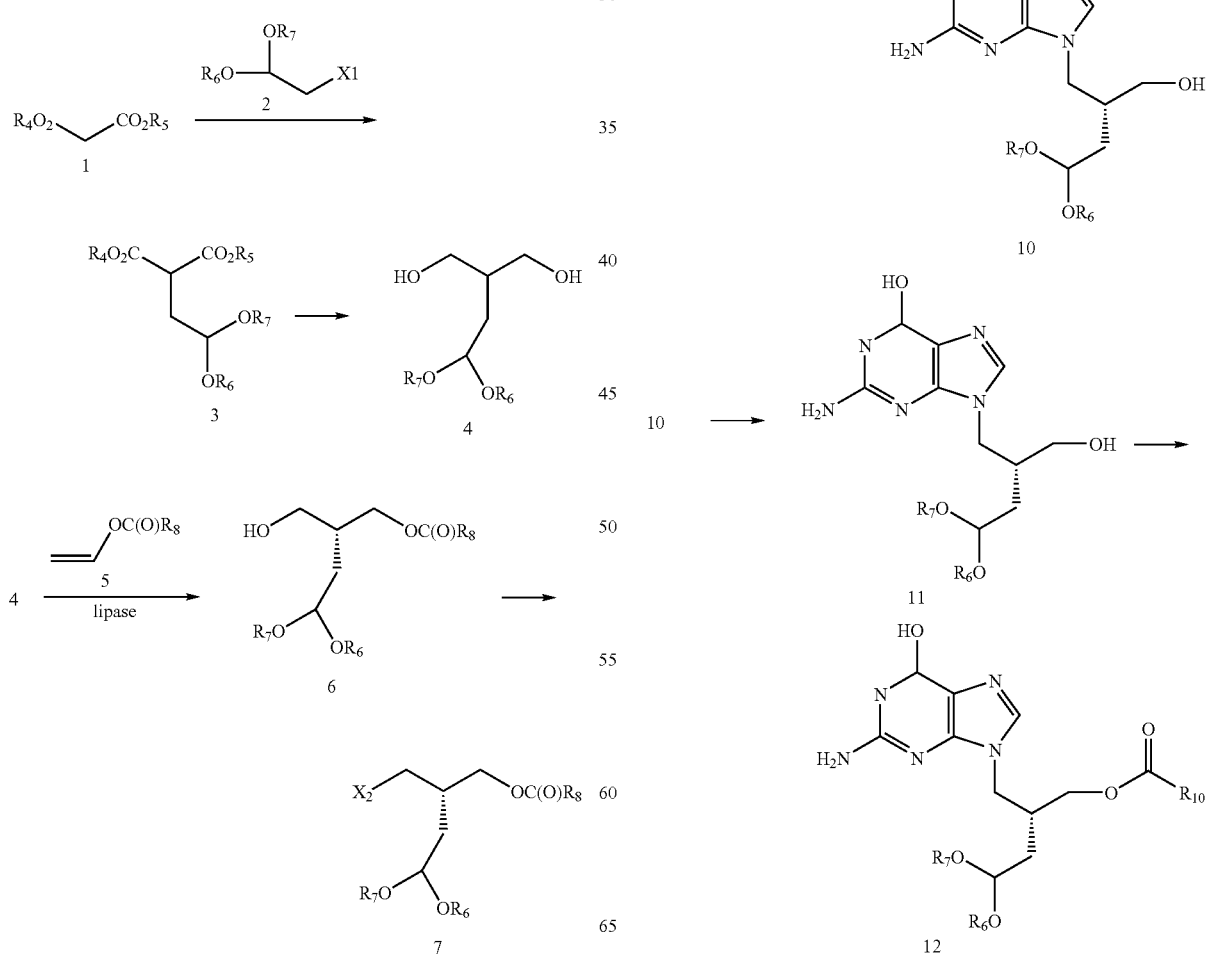

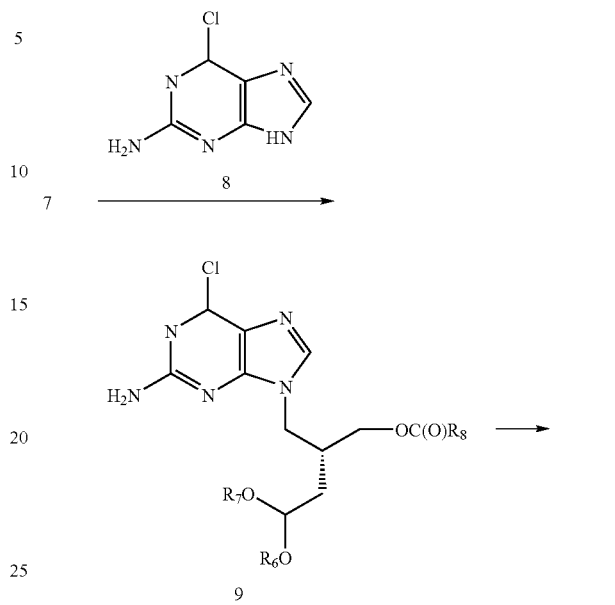

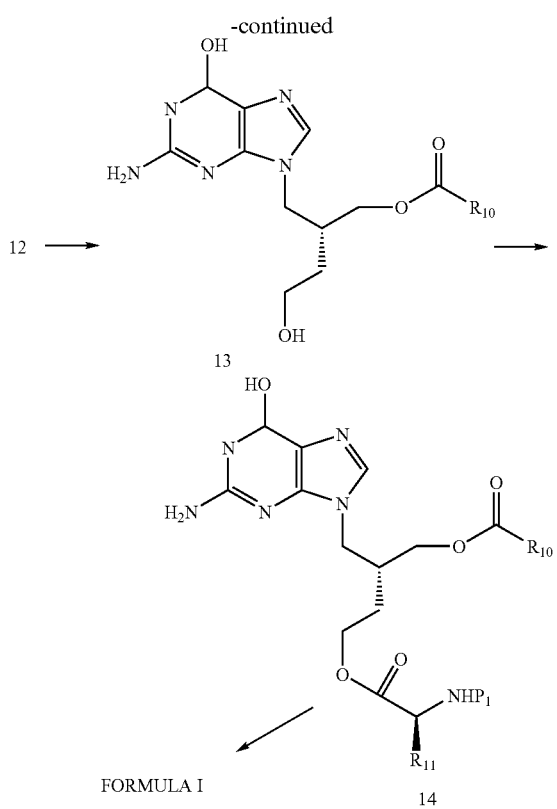

FORMULA I

Referring to Scheme C, malonate 1 ($R_4$ and $R_5$ are lower alkyl or benzyl or the like) is alkylated by reaction with from about 0.5 to about 2.0 molar equivalents of acetal 2 ($R_6$ and $R_7$ are lower alkyl or benzyl and the like or $R_6$ and $R_7$ taken together are —$CH_2CH_2$— or —$CH_2CH_2CH_2$— or —$CH_2CH_2CH_2CH_2$-and $X_1$ is a leaving group (for example, Cl, Br or I, or a sulfonate such as methanesulfonate, triflate, p-toluenesulfonate, benzenesulfonate and the like)) in the presence of from about 0.5 to about 2.0 molar equivalents of a base (for example, potassium t-butoxide or sodium ethoxide or NaH or KH and the like) in an inert solvent (for example, DMF or THF or dioxane or dioxolane or N-methylpyrrolidone and the like) at a temperature of from about −40° C. to about 190° C. to provide alkylated malonate 3.

Reduction of 3 with from about 0.5 to about 4.0 molar equivalents of an ester to alcohol reducing agent (for example, $LiBH_4$ or $Ca(BH_4)_2$ or $NaBH_4$ or $LiAlH_4$ and the like) in an inert solvent (for example, THF or methyl t-butyl ether or t-BuOH and the like) at a temperature of from about −20° C. to about 1 00° C. provides diol 4. Enzymatic esterification of 4 by reaction with from about 1.0 to about 20.0 molar equivalents of a vinyl ester 5 ($R_8$ is $C_3$-$C_{21}$ saturated or monounsaturated, optionally substituted alkyl) in the presence of a lipase (for example, Lipase PS-30 or Lipase PPL or Lipase CCL and the like) or a phospholipase (for example phospholipase D and the like) provides the desired stereoisomer of ester 6. This reaction can be carried out in the absence of solvent or in the presence of an inert solvent (for example, methyl t-butyl ether or toluene or hexane and the like). The reaction is carried out at a temperature of from about −20° C. to about 80° C.

The alcohol substituent of 6 is converted to a leaving group (for example, a halogen or a sulfonate) by reaction with a halogenating agent (for example NBS/P(Ph)$_3$ or NCS/P(Ph)$_3$ or POCl$_3$ or NCS/P(Ph)$_3$/NaI in acetone and like) in an inert solvent (for example, methylene chloride or toluene or ethylacetate and the like) or by reaction with from about 0.8 molar equivalents to about 2.0 molar equivalents of a sulfonyl halide (for example, benzenesulfonylchloride, toluenesulfonylchloride or methane sulfonylchloride and the like) in the presence of from about 1.0 to about 4.0 molar equivalents of a base (for example, triethylamine or potassium carbonate or pyridine or dimethylaminopyridine or ethyldiisopropylamine and the like) in an inert solvent (for example methylene chloride or toluene or ethylacetate or pyridine or methyl t-butyl ether and the like) at a temperature of from about −25° C. to about 100° C. to provide ester 7. ($X_2$ is a halogen or sulfonate leaving group).

Reaction of 7 with from about 0.9 to about 2.0 molar equivalents of 2-amino-4-chloropurine 8 in the presence of from about 1.0 to about 6.0 molar equivalents of a base (for example, potassium carbonate or NaH or KH or NaOH or KOH or lithium diisopropylamide and the like) in an inert solvent (for example, DMF or THF or acetonitrile or N-methylpyrrolidone or ethanol and the like) at a temperature of from about −25° C. to about 140° C. provides substituted purine 9.

Alternatively Mitsunobu coupling (for example P(Ph)$_3$/diethyl azidocarboxylate) of alcohol 6 with 2-amino-4-chloropurine 8 provides 9.

Reaction of 9 with from about 2.0 to about 20 molar equivalents of an alcohol $R_9OH$($R_9$ is an alcohol protecting group such as benzyl and the like) in the presence of from about 1.0 to about 6.0 molar equivalents of a base (for example, potassium t-butoxide or potassium carbonate or NaH or KH or lithium diisopropylamide and the like) in an inert solvent (for example, THF or DMF and the like) at a temperature of from about −25° C. to about 150° C. provides alcohol 10.

Removal of the alcohol protecting group $R_9$ of 10 (for example, by catalytic hydrogenation in an inert solvent such as ethanol or benzyl alcohol or methanol or THF and the like in the presence of an hydrogenation catalyst such as Pd/C or Pd(OH)$_2$ and the like) provides substitued guanine 11.

Esterification of 11 by reaction with a) from about 0.8 to about 2.0 molar equivalents of $R_{10}$COOH and a coupling agent (for example DCC/DMAP) and the like in an inert solvent (for example THF or DMF and the like) or b) from about 0.8 to about 2.0 molar equivalents of an activated derivative of $R_{10}$COOH (for example, the acid chloride or N-hydroxysuccinimide ester or $R_{10}$C(O)OC(O)$R_{10}$ and the like) in the presence of from about 0 to about 3.0 molar equivalents of a base (for example, pyridine or triethylamine or ethyldiisopropylamine or DBU or potassium carbonate and the like) in an inert solvent (for example, methylene chloride or THF or pyridine or acetonitrile or DMF and the like) at a temperature of from about −25° C. to about 100° C. provides ester 12.

The acetal substituent of 12 is deprotected and the resulting aldehyde is reduced by first reacting 12 with from about 0.1 to about 10.0 molar equivalents of an acid (for example, triflic acid or HCl or acetic acid or sulfuric acid and the like) in an inert solvent (for example, THF/H$_2$O or methylene chloride/H$_2$O or ethylacetate/H$_2$O or ethanol/H$_2$O or methanol/H$_2$O and the like) at a temperature of from about −25° C. to about 1 00° C. To the crude reaction mixture is added from about 0.1 to about 10.0 molar equivalents of a base (for example, sodium bicarbonate or potassium carbonate or triethylamine or pyridine or KOH and the like), additional inert solvent (for example, THF and or methylene chloride or ethylacetate or methyl t-butyl ether or isopropoanol and the like) and from about 0.3 to about 5.0 molar equivalents of an aldehyde reducing agent (for example, sodium borohydride or RaNi/H$_2$ and the like) at a temperature of from about −25° C. to about 100° C. to provide alcohol 13.

Reaction of 13 with from about 0.8 to about 3.0 molar equivalents of N-protected amino acid P$_1$NHCH(R$_{11}$)COOH or an activated derivative thereof (P$_1$ is an N-protecting group and R$_{11}$ is isopropyl or isobutyl) in an inert solvent (for example, THF or dioxane or dioxolane or DMF or methylene chloride and the like) at a temperature of from about 25° C. to about 100° C. provides alcohol 14. N-deprotection of 14 provides the compound of the invention of formula I wherein R$_3$ is —OH.

Alternatively compound 13 can be reacted with the symmetrical anhydride derived from P$_1$NHCH(R$_{11}$)COOH (i.e. P$_1$NHCH(R$_{11}$)C(O)O—C(O)CH(R$_{11}$)NHP$_1$) to provide 1 wherein R$_3$ is OH.

Another alternative process for the preparation of compounds wherein R$_3$ is —OH is shown in Scheme D.

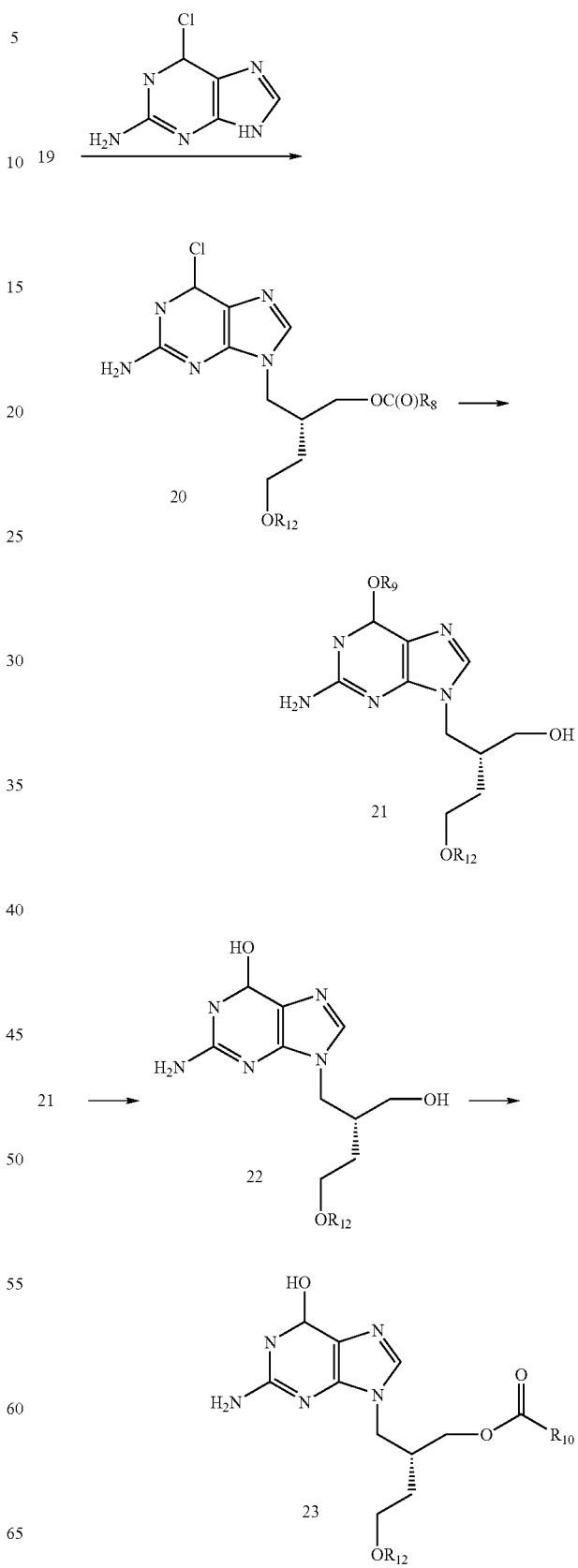

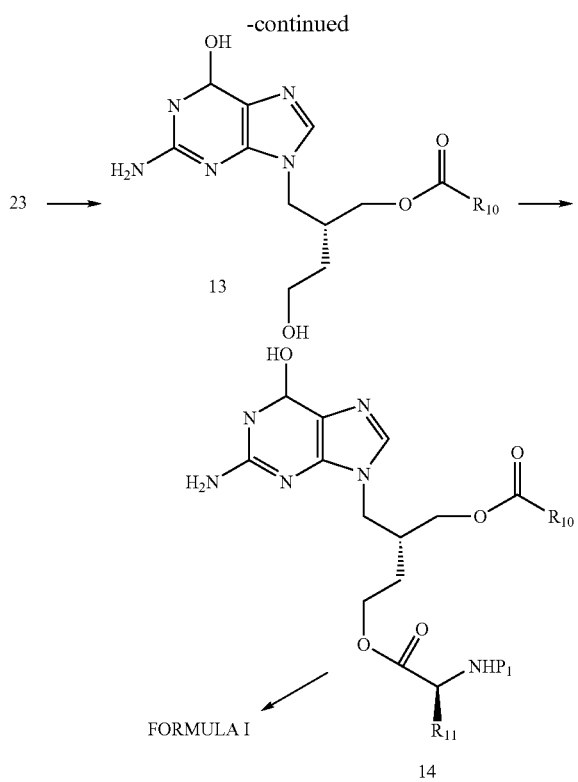

Malonate 1 ($R_4$ and $R_5$ are lower alkyl or benzyl and the like) is alkylated with from about 0.5 to about 2.0 molar equivalents of ether 15 wherein X, is a leaving group (for example Cl, Br or I, or a sulfonate such as methane sulfonate, triflate, p-toluenesulfonate, benzenesulfonate and the like) and $R_{12}$ is —CH(Ph)$_2$, —C(Ph)$_3$ or —Si(t-Bu)(Me)$_2$ and the like (Ph=phenyl) in the presence of from about 0.5 to about 2.0 molar equivalents of a base (for example potassium t-butoxide or sodium ethoxide or NaH or KH and the like) in an inert solvent (for example DMF or THF or dioxane or dioxolane or N-methyl pyrrolidinone and the like) at a temperature of from about −40° C. to about 190° C. to provide alkylated malonate 16.

Reduction of 16 with from about 0.5 to about 4.0 molar equivalents of an ester to alcohol reducing agent (for example LiBH$_4$ or Ca(BH$_4$)$_2$ or NaBH$_4$ or LiAlH$_4$ and the like) in an inert solvent (for example THF or methyl t-butyl ether or ethanol or t-butanol and the like) at a temperature of from about −20° C. to about 1 00° C. provides diol 17. Enzymatic esterification of 17 by reaction with from about 1.0 to about 20.0 molar equivalents of a vinyl ester 5 ($R_8$ is $C_3$-$C_2$, saturated or monounsaturated, optionally substituted alkyl) in the presence of a lipase (for example, Lipase PS-30 or Lipase PPL or Lipase CCL and the like) or a phospholipase (for example phospholipase D and the like) provides the desired stereoisomer of ester 18. The reaction can be carried out in the absence of solvent or in the presence of an inert solvent (for example methyl t-butyl ether or toluene or hexane or the like). The reaction is carried out at a temperature of from about −20° C. to about 80° C.

The alcohol substituent of 18 is converted to a leaving group (for example a halogen or sulfonate) by reaction with a halogenating agent (for example NBS/P(Ph)$_3$ or NCS/P(Ph)$_3$ or POCl$_3$ or NCS/P(Ph)$_3$/NaI in acetone and the like) in an inert solvent (for example methylene chloride or toluene or ethylacetate and the like) or by reaction with from about 0.8 molar equivalents to about 2.0 molar equivalents of a sulfonyl halide (for example benzenesulfonylchloride, toluenesulfonylchloride or methane sulfonylchloride and the like) in the presence of from about 1.0 to about 4.0 molar equivalents of a base (for example triethylamine or potassium carbonate or pyridine or methyl t-butyl ether and the like) at a temperature of from about −25° C. to about 100° C. to provide ester 19. ($X_2$ is a halogen or sulfonate leaving group).

Reaction of 19 with from about 0.9 to about 2.0 molar equivalents of 2-amino-4-chloropurine 8 in the presence of from about 1.0 to about 6.0 molar equivalents of a base (for example potassium carbonate or NaH or KH or NaOH or KOH or lithium diisopropylamide and the like) in an inert solvent (for example DMF or THF or acetonitrile or N-methylpyrrolidone or ethanol and the like) at a temperature of from about −25° C. to about 140° C. provides substituted purine 20.

Alternatively, Mitsunobu coupling (for example, P(PH)$_3$/ diethyl azidocarboxylate) of alcohol 18 with 2-amino-4-chloropurine 8 provides 20.

Reaction of 20 with from about 2.0 to about 20.0 molar equivalents of an alcohol R$_9$OH (R$_9$ is an alcohol protecting group such as benzyl and the like) in the presence of from about 1.0 to about 6.0 molar equivalents of a base (for example, potassium t-butoxide or potassium carbonate or NaH or KH or lithium diisopropylamide and the like in an inert solvent (for example, THF or DMF and the like) at a temperature of from about −25° C. to about 150° C. provides alcohol 21.

Removal of the alcohol protecting group R$_9$ of 21 (for example by catalytic hydrogenation in an inert solvent such as ethanol or benzyl alcohol or methanol or THF and the like in the presence of an hydrogenation catalyst such as Pd/C or Pd(OH)$_2$ and the like) provides substituted guanine 22.

The ether substituent of 23 is deprotected by reaction with a) a reducing agent (for example, HCO$_2$H and Pd/C and the like) wherein $R_{12}$ is —CH(Ph)$_2$ or —C(Ph)$_3$, or b) a desilylating agent (for example Bu$_4$NF and the like) wherein $R_{12}$ is —Si(t-Bu)(Me)$_2$ and the like to provide 13.

Alcohol 13 can be converted to 1 as outlined in scheme C.

An additional alternative involves enzymatic esterification of alcohol 4 or 17 with the vinyl ester CH$_2$=CH—OC(O)$_{10}$ (i.e. R$_8$=R$_{10}$ in Schemes C and D) to directly incorporate into 6 or 18 the desired carboxylic acid ester of the final product I. This allows the elimination of the ester hydrolysis and reesterification involved in going from 9 to 12 or from 20 to 23.

The processes of Schemes C and D are characterized by the fact that each of the hydroxyl groups of the acyclic side chain is differentiated by the use of different hydroxy protecting groups or precursor groups. This allows the selective acylation of each of the hydroxy groups with either an amino acid or a fatty acid group.

Schemes C and D have been illustrated and described with reference to embodiments of the invention wherein $R_1$ is derived from an amino acid and $R_2$ is derived from a fatty acid. However, it will be apparent that respective converse schemes will apply to compounds where $R_1$ is derived from a fatty acid and $R_2$ is derived from an amino acid.

DETAILED DESCRIPTION OF THE INVENTION

The invention will now be illustrated by way of example only with reference to the following non-limiting Examples, comparative examples and the accompanying Figures, in which:

EXAMPLE 1

(R)-9-[2-(Stearoyloxymethyl)-4-(L-valyloxy)butyl] guanine

Figure 1:
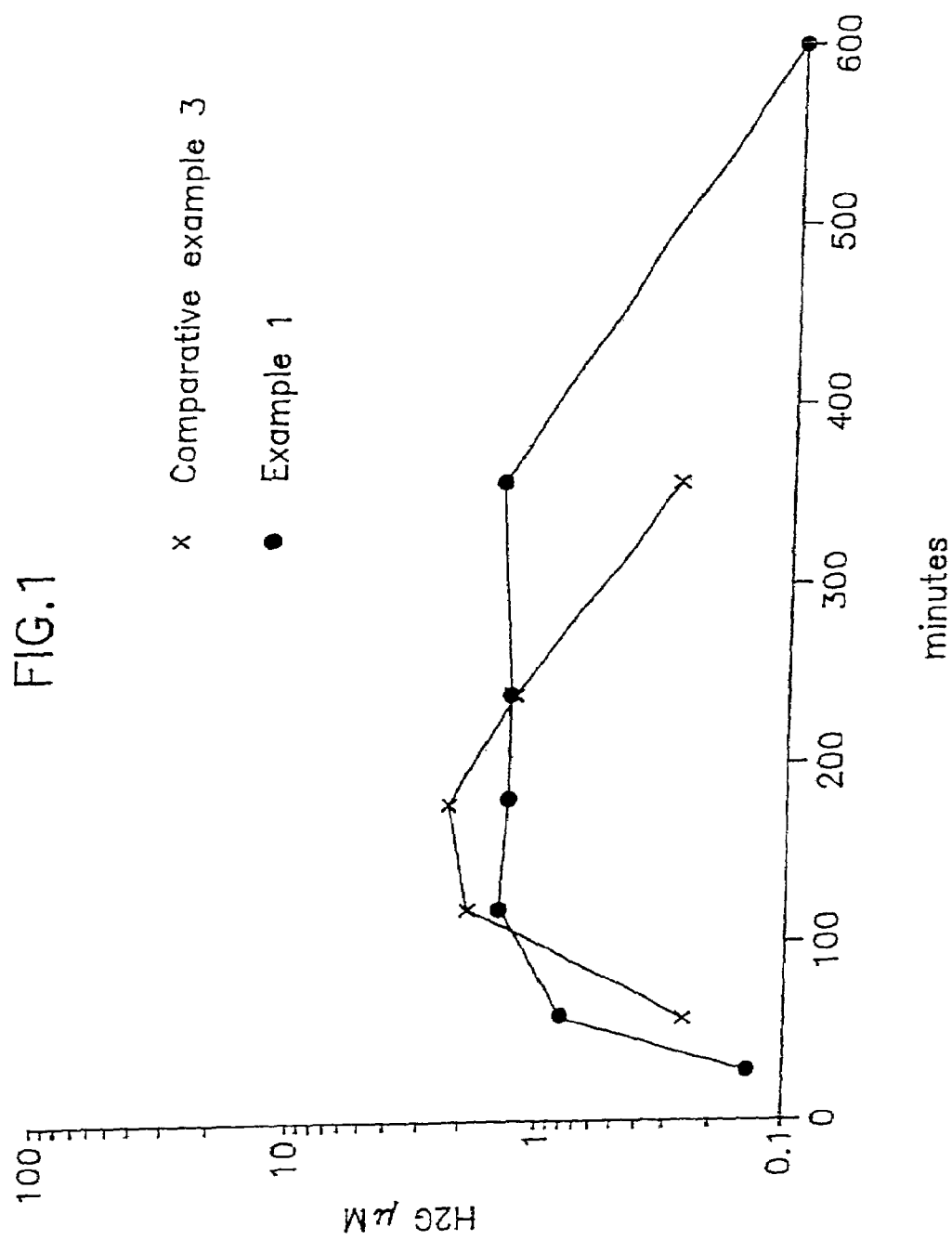
FIG. 1 depicts plasma H2G levels as a function of time in cynomolgus monkeys administered with a compound of the invention or with an alternative prodrug derivative of H2G, as further explained in Biological Example 3.

This example illustrates the application of preparation scheme A.

a) (R)-9-[4-(N-tert-Butoxycarbonyl-L-valyloxy)-2-(hydroxymethyl) butyl]guanine.

H2G (5 g, 19.7 mmol) was dissolved in DMF (300 ml) under heating and was cooled to room temperature before addition of N-t-Boc-L-valine (5.58 g, 25.7 mmol), DMAP (0.314 g, 2.57 mmol) and DCC (6.52 g, 31.6 mmol). The mixture was stirred at room temperature for 24 h and was then filtered. The product was chromatographed on silica gel and eluted with $CH_2Cl_2$/MeOH to give 2.4 g of the desired intermediate product.

$^1$H-NMR (250 MHz, DMSO-$d_6$): δ 0.95 (d, 6H), 1.47 (s, 9H), 1.5-1.8 (m, 2H), 1.96-2.20 (m, 2H), 3.40 (m, 2H), 3.91 (t, 1H), 4.05 (m, 2H), 4.21 (t, 2H), 4.89 (t, 1H), 6.6 (br s, 2H), 7.27 (d, 1H), 7.75 (s, 1H), 10.7 (br s, 1H).

b) (R)-9-[4-(N-tert-Butoxycarbonyl-L-valyloxy)-2-(stearoyloxymethyl) butyl]guanine The product from step a) (185 mg, 0.41 mmol) was dissolved in pyridine (5 ml), the solution was cooled in an ice bath and stearoyl chloride (179 μl, 0.531 mmol) was added. The solution was kept in the ice bath for 2 h, then at room temperature for 1 h. It was then evaporated and chromatographed on silica gel. It was eluted with dichloromethane/methanol to give 143 mg of the desired intermediate product.

c) (R)-9-[2-(Stearoyloxymethyl)-4-(L-valyloxy)butyl]guanine.

The product from step b) (138 mg, 0.192 mmol) was cooled in an ice bath and trifluoroacetic acid (5 ml) was added. The solution was kept in the ice bath for 45 minutes and was then evaporated to give an oil. Water (0.5 to 1 ml) was added and evaporated twice. The residue was once more dissolved in water (5 ml), filtered and freeze-dried to give 148 mg of the desired product as the bistrifluoracetate salt.

$^1$H NMR (250 MHz, DMSO-$d_6$): 0.97 (t, 3H), 1.05 (dd, 6H), 1.34 (br s, 28H), 1.59 (m, 2H), 1.80 (m, 2H), 2.25 (m, 1H), 2.36 (t, 2H), 2.50 (m, 1H), 3.98-4.18 (m, 5H), 4.35 (t, 2H), 6.6 (br s, 2H), 8.0 (br s, 1H), 8.4 (br s, 3H), 10.9 (br s, 1H).

EXAMPLE 2

(R)-9-[2-(Myristoyloxymethyl)-4-(L-valyloxy)butyl] guanine

The titled compound was obtained as the bistrifluoracetate salt in a manner analogous to Example 1 using myristoyl chloride instead of stearoyl chloride in step b).

$^1$H NMR (250 MHz, DMSO-$d_6$): δ 0.97 (t, 3H), 1.05 (dd, 6H), 1.34 (br s, 20H), 1.57 (m, 2H), 1.78 (m, 2H), 2.24 (m, 1H), 2.35 (t, 2H), 2.51 (m, 1H), 3.97-4.20 (m, 5H), 4.36 (t, 2H), 6.8 (br s, 2H), 8.2 (br s, 1H), 8.5 (br s, 3H), 11.1 (br s, 1H).

EXAMPLE 3

(R)-9-[2-(Oleoyloxymethyl)-4-(L-valyloxy)butyl] guanine

The titled compound was obtained as the bistrifluoroacetyl salt in a manner analogous to Example 1 using oleoyl chloride instead of stearoyl chloride in step b).

$^1$H NMR (250 MHz, DMSO-$d_6$): 0.96 (t, 3H), 1.05 (dd, 6H), 1.35 (br s, 20H), 1.59 (m, 2H), 1.76 (m, 2H), 2.09 (m, 4H), 2.24 (m, 1H), 2.35 (t, 2H), 2.50 (m, 1H), 3.97-4.17 (m, 5H), 4.35 (t, 2H), 5.43 (t, 2H), 6.7 (br s, 2H), 8.0 (br s, 1H), 8.5 (br s, 3H), 11.1 (br s, 1H).

EXAMPLE 4

(R)-9-[2-(Butyryloxymethyl)-4-(L-valyloxy)butyl] guanine a) (R)-9-[4-(N-tert-Butoxycarbonyl-L-valyloxy)-2-(butyryloxymethyl) butyl]guanine DCC (110 mg, 0.53 mmol) was dissolved in dichloromethane (10 ml) and butyric acid (82 mg, 0.93 mmol) was added. After 4 hours at room temperature the mixture was filtered and the filtrate was evaporated. The residue was dissolved in pyridine (5 ml) and (R)-9-[4-(N-tert-Butoxycarbonyl-L-valyloxy)-2-hydroxymethylbutyl] guanine (200 mg, 0.44 mmol) (Example 1, step a) was added. The mixture was stirred for 120 hours at room temperature. According to TLC the reaction was incomplete and more anhydride was made using the procedure above. This anhydride was added and the mixture was stirred for an additional 20 hours. The reaction mixture was evaporated and chromatographed first on silica gel and then on aluminium oxide, in both cases eluted with dichloromethane/methanol to give 79 mg of the intermediate product.

b) (R)-9-[2-(Butyryloxymethyl)-4-(L-valyloxy)butyl]guanine

The intermediate product of step a was deprotected in a manner analogous to Example 1, step 3 to give 84 mg of the desired product as the bistrifluoracetate salt.

$^1$H NMR (250 MHz, D$_2$O): δ 0.88 (t, 3H), 1.06 (dd, 6H), 1.53 (m, 2H), 1.93 (q, 2H), 2.25 (t, 2H), 2.36 (m, 1H), 2.60 (m, 1H), 4.06 (d, 1H), 4.14-4.30 (m, 2H), 4.43 (m, 4H), 8.99 (br s, 1H).

EXAMPLE 5

(R)-9-[2-(Decanoyloxymethyl)-4-(L-valyloxy)butyl] guanine

The titled compound was obtained as the bistrifluoroacetate salt in a manner analogous to Example 1 using decanoyl chloride instead of stearoyl chloride in step b.

$^1$H NMR (250 MHz, D$_2$O): δ 0.90 (m, 3H), 1.01 (d, 6H), 1.28 (br s, 12H), 1.5 (m, 2H), 1.8 (m, 2H), 2.3 (m, 3H), 2.5 (m, 1H), 4.0-4.4 (m, 7H), 8.1 (br s, 1H).

EXAMPLE 6

(R)-9-[2-Docosanoyloxymethyl-4-(L-valyloxy)butyl] guanine

The titled compound was obtained as the bistrifluoroacetate salt in a manner analogous to Example 1 but using in step b the DMAP/DCC conditions of Example 1, step a) in conjunction with docosanoic acid in place of the N-t-Boc-L-valine and a mixture of DMF and dichloromethane as solvent.

$^1$H NMR (250 MHz, DMSO-$d_6$): δ 0.97 (t, 3H), 1.05 (dd, 6H), 1.34 (br s, 36H), 1.58 (m, 2H), 1.77 (m, 2H), 2.24 (m, 1H), 2.35 (t, 2H), 2.50 (m, 1H), 3.97-4.17 (m, 5H), 4.35 (t, 2H), 6.7 (br s, 2H), 8.1 (br s, 1H), 8.4 (br s, 3H), 11.0 (br s, 1H).

EXAMPLE 7

R-9-[4-(L-Isoleucyloxy)-2-(stearoyloxymethyl)butyl]guanine

This example illustrates the application of preparative scheme B.

a) (R)-9-[2-hydroxymethyl 4-(t-butyldiphenylsilyloxy)butyl]guanine

H2G (2 g, 8 mmole) was coevaporated with dry DMF two times and was then suspended in dry DMF (120 ml) and pyridine (1 ml). To the suspension was added dropwise t-butyldiphenylchlorosilane (2.1 ml, 8.2 mmole) in dichloromethane (20 ml) at 0° C. over a period of 30 min. The reaction mixture became a clear solution at the completion of the dropwise addition. The reaction continued at 0° C. for two hours and was then kept at 4° C. overnight. Methanol (5 ml) was added to the reaction. After 20 min at room temperature, the reaction mixture was evaporated to a small volume, poured into aqueous sodium hydrogen carbonate solution and extracted with dichloromethane two times. The organic phase was dried over sodium sulphate and evaporated in vacuo. The product was isolated by silica gel column chromatography using a methanol/dichloromethane system with a stepwise increasing MeOH concentration. The product was eluted with 7% MeOH in $CH_2Cl_2$ to yield 1.89 g.

b) (R)-9-[2-(Stearoyloxymethyl)-4-(t-butyldiphenylsilyloxy)butyl]guanine (R)-9-[2-Hydroxymethyl 4-(t-butyldiphenylsilyloxy)butyl]guanine (2.31 g, 5 mmole) was coevaporated with dry pyridine twice and dissolved in pyridine (20 ml). To the solution was slowly added dropwise stearoyl chloride (1.86 ml, 5.5 mmole, technical grade) in dichloromethane (2 ml) at −5° C. The reaction was kept at the same temperature for 1 hr and then at 5° C. for 2 hr. The reaction was monitored by TLC. Additional stearoyl chloride (0.29 ml) at −5° C. was added due to incompletion of reaction. After 30 min at 5° C., methanol (3 ml) was added and the reaction mixture stirred for 20 min. It was then poured into aqueous sodium hydrogen carbonate solution, and extracted with dichloromethane. The organic phase was dried and the product purified by silica ge column chromatography with stepwise increasing MeOH, eluting with 3.5% MeOH in $CH_2Cl_2$ (Yield 2.7 g).

c) (R)-9-[(4-Hydroxy-2-(stearoyloxymethyl)butyl]guanine (R)-9-[2-(Stearoyloxymethyl)-4-(t-butyldiphenylsilyloxy)butyl]guanine (2.7 g, 3.56 mmole) was dissolved in dry THF (30 ml) and hydrogen fluoride-pyridine (1.5 ml) added to the solution. The reaction was kept at 4° C. overnight and monitored by TLC. The reaction reached about 80% conversion. Additional HF-pyridine was added (0.75 ml). After 4 hr, TLC showed that the starting material had disappeared. The reaction mixture was concentrated in vacuo without raising the temperature and more pyridine (5 ml) was added and evaporated again. The product was isolated by silica gel column chromatography. (Yield 1.26 g).

d) (R)-9-[4-(N-BOC-L-isoleucyloxy)-2-(stearoyloxymethyl)butyl]guanine (R)-9-[4-Hydroxy-2-(stearoyloxymethyl)butyl] guanine (135 mg, 0.26 mmole) and N-BOC-L-isoleucine (180 mg, 0.78 mmole) were coevaporated with dry DMF twice and dissolved in-the same solvent (3.5 ml). To the solution was added 1,3-dicyclohexylcarbodiimide (160 mg, 0.78 mmole) and 4-dimethylaminopyridine (4.8 mg, 0.039 mmole). After reaction for 18 hours, the reaction mixture was filtered through Celite and worked up in a conventional manner. The product was isolated by silica gel column chromatography, eluting at 5% MeOH in $CH_2Cl_2$. (Yield 160 mg)

e) (R)-9-[4-(L-Isoleucyloxy)-2-(stearoyloxymethyl)-butyl]guanine (R)-9-[4-(N-BOC-L-isoleucyloxy)-2-(stearoyloxymethyl)butyl]guanine (150 mg, 0.205 mmole) from step d) was treated with trifluoroacetic acid (3 ml) at 0° C. for 20 min. The solution was evaporated in vacuo. The residue was coevaporated with toluene twice and kept under vacuum for several hours. The residue was dissolved in MeOH (2 ml) and evaporated to give the trifluoracetate salt as a glass-like product (Yield 191 mg).

$H^1$ NMR (DMSO-$d_6$+$D_2O$): δ 8.35 (s,1H, base), 4.21 (t, 2H, H-4), 4.10 (d, 2H) 3.96 (d, 2H), 3.90 (d, 1H, isoleucine), 2.48 (m, 1H, H-2), 2.15 (2H, stearoyl), 1.85 (m, 1H, isoleucine), 1.68 (m, 2H), 1.48 (m, 4H), 1.68 (m, 28H), 0.81 (m, 9H).

EXAMPLE 8

(R)-9-[2-(Decanoyloxymethyl)-4-(L-isoleucyloxy)butyl]guanine

The title compound was obtained as the bistrifluoroacetyl salt in a manner analogous to Example 7 using decanoyl chloride instead of stearoyl chloride in step b).

$^1$H NMR (DMSO-d6): δ 11.1 (s, 1H, NH), 8.35 (s, br, 3H), 8.28 (s, 1H, base), 6.75 (s, 2H, $NH_2$), 4.23 (t, 2H), 4.07 (d, 2H), 4.05 (m, 3H), 2.4 (m, 1H), 2.21 (t, 2H), 1.83 (m, 1H), 1.66 (m, 2H), 1.45 (m, 2H), 1.39 (m, 2H), 1.22 (s, 12H), 0.84 (m, 9H).

EXAMPLE 9

(R)-9-[4-(L-Isoleucyloxy)-2-(myristoyloxymethyl) butyl]guanine

The title compound was obtained as the bistrifluoroacetyl salt in a manner analogous to Example 1 using N-BOC-L-isoleucine instead of N-BOC-valine in step a) and myristoyl chloride in step b).

$^1$H-NMR (DMSO-d6): δ 10.99(s, 11H), 8.34 (br s, 3H) 8.15 (s, 1H), 6.67 (br s, 2H), 4.23 (t, 2H), 4.05 (d, 2H), 3.97 (m, 3H), 2.48 (m, 1H), 2.20 (t, 2H), 1.85 (m, 1H), 1.65 (m, 2H), 1.41 (m, 4H), 1.23 (s, 20H), 0.85 (m, 9H).

EXAMPLE 10

(R)-9-[2-(4-Acetylbutyryloxymethyl-4-(L-valyloxy)butyl]guanine

The titled compound was obtained as the bistrifluoroacetate salt in a manner analogous to Example 1 but using in step b) the DCC/DMAP conditions of Example 1, step a) in conjunction with 4-acetylbutyric acid instead of N-t-Boc-L-valine.

$^1$H-NMR (250 MHz, DMSO-$d_6$): δ 1.05 (dd, 6H), 1.77 (m, 4H), 2.19 (s, 3H), 2.24 (m, 1H), 2.36 (t, 2H), 2.44-2.60 (m, 3H), 3.95-4.20 (m, 5H), 4.36 (m, 2H), 6.8 (br s, 2H), 8.3 (br s, 1H), 8.5 (br s, 3H), 11.1 (br s, 1H).

EXAMPLE 11

(R)-9-[2-Dodecanoyloxymethyl-4-(L-valyloxy)butyl]guanine

The titled compound was obtained as the bistriflouroacetate salt in a manner analogous to Example 1 using dodecanoyl chloride instead of stearoyl chloride in step b).

EXAMPLE 12

(R)-9-[2-Palmitoyloxymethyl-4-(L-valyloxy)butyl]guanine

The titled compound was obtained as the bistriflouroacetate salt in a manner analogous to Example 1 using palmitoyl chloride instead of stearoyl chloride in step b).

$^1$H-NMR(250 MHz, DMSO-$d_6$): δ 0.97 (t, 3H), 1.05 (m, 6H), 1.35 (br s, 24H), 1.58 (m, 2H), 1.78 (m, 2H), 2.25 (m, 1H), 2.35 (t, 2H), 2.51 (m, 1H), 3.97-4.18 (m, 5H), 4.35 (t, 2H), 6.7 (br s, 2H), 8.1 (br s, 1H), 8.5 (br s, 3H), 11.0 (br s, 1H).

EXAMPLE 13

(R)-2-Amino-9-(2-stearoyloxymethyl-4-(L-valyloxy)butyl)purine

This example shows the deoxygenation of group $R_1$.

a) (R)-2-Amino-9-(2-stearoyloxymethyl-4-(N-tert-butoxycarbonyl-L-valyloxy)butyl)-6-chloropurine:

To a solution of (R)-9-(2-stearoyloxymethyl-4-(N-tert-butoxycarbonyl-L-valyloxy)butyl)guanine from step 2 of Example 1 (646 mg, 0.9 mmole) in acetonitrile were added tetramethylammonium chloride (427 mg, 2.7 mmole), N,N-diethylaniline (0.716 ml, 4.5 mmole) and phosphorous oxychloride (0.417 ml, 4.5 mmole). The reaction was kept under reflux and the progression monitored by TLC. After 3 hours the reaction mixture was evaporated in vacuo and the residue was dissolved in dichloromethane, then poured into cold sodium hydrogen carbonate aqueous solution. The organic phase was evaporated and purified by silica gel column chromatography. Yield: 251 mg.

$H^1$-NMR (CDCL$_3$): δ 7.76 (1H, H-8), 5.43 (br,2H, NH$_2$), 4.45-4.00 (m, 7H), 2.53 (m, 1H), 2.28 (t 2H), 2.12 (m, 1H), 1.75 (m, 2H), 1.59 (m, 2H), 1.43 (9H), 1.25 (m, 28H), 0.96 (d, 3H), 0.87 (m, 6H).

b) (R)-2-Amino-9-(2-stearoyloxmethyl-4-(N-tert-butoxycarbonyl-L-valyloxy)butyl)purine:

To the solution of (R)-2-amino-9-(2-stearoyloxymethyl-4-(N-tert-butoxycarbonyl-L-valyloxy)butyl)-6-chloropurine (240 mg, 0.33 mmole) in methanol/ethyl acetate (6 ml, 3:1 V/V) were added ammonium formate (105 mg, 1.65 mmole) and 10% palladium on carbon (15 mg). The reaction was kept under reflux for 1 hour and recharged with ammonium formate (70 mg). After one hour more the TLC showed completion of the reaction and the mixture was filtered through Celite and washed extensively with ethanol. The filtrate was evaporated and purified by silica gel column. Yield: 193 mg.

$H^1$-NMR (CDCL$_3$): δ8.69 (s,1H, H-6), 7.74 (s, 1H, H-8), 5.18 (br, s, 2H, NH$_2$), 4.45-4.01 (m, 7H), 2.55 (m, 1H), 2.28 (t, 2H), 2.10 (m, 1H), 1.75 (m, 2H), 1.60 (m, 2H), 1.43 (s, 9H), 1.25 (s, 28H), 0.96 (d, 3H), 0.87 (m, 6H).

c) (R)-2-Amino-9-(2-stearoyloxymethyl-4-(L-valyloxy)butyl)purine:

(R)-2-Amino-9-(2-Stearoyloxmethyl-4-(N-tert-butoxycarbonyl-L-valyloxy)butyl)purine (180 mg, 0.26 mmole) was treated with trifluoroacetic acid (5 ml) at 0° C. for 40 min. It was then evaporated in vacuo and coevaporated successively with toluene and methanol. The residue was freeze-dried overnight to give 195 mg of the desired product.

$^1$H-NMR (DMSO-$d_6$): δ 8.78 (s, 1H, H-6), 8.32 (br, 3H), 8.29 (s, 1H, H-8), 4.27 (t, 2H), 4.13 (d, 2H), 3.98 (t, 2H, 2H), 3.89 (m, 1H), 2.47 (m, 1H), 2.18 (m, 3H), 1.43 (m, 2H), 1.23 (28H), 0.93 (m, 6H), 0.85 (t, 3H).

EXAMPLE 14

Alternative Preparation of (R)-9-[4-Hydroxy-2-(stearoyloxymethyl)butyl]guanine a) Preparation of ethyl 4,4-diethoxy-2-ethoxycarbonyl-butyrate

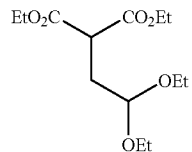

Potassium tert-butoxide (141.8 g, 1.11 equiv.) was dissolved in dry DMF (1 L). Diethyl malonate (266 mL, 1.54 equiv.) was added over 5 minutes. Bromoacetaldehyde diethylacetal (172 mL, 1.14 mole) was added over 5 minutes. The mixture was heated to 120° C. (internal temperature), and stirred at 120° C. for 5 hours. The mixture was allowed to cool to room temperature, poured into water (5 L), and extracted with methyl tert-butyl ether (MTBE, 3×600 mL). The organic solution was dried over MgSO$_4$, filtered, concentrated, and distilled (0.5 mm, 95-140° C.) to yield the desired diester (244 g, 78%) as a colorless oil.

$^1$H NMR (CDCl$_3$) δ 1.19 (t, 6H), 1.28 (t, 6H), 2.22 (dd, 2H), 3.49 (m, 2H), 3.51 (t, 1H), 3.65 (m, 2H) 4.20 (qd, 4H), 4.54 (t, 1H).

b) Preparation of 4,4-diethoxy-2-(hydroxymethyl)-butanol

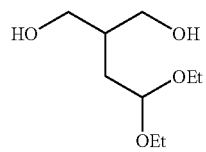

LiBH4 (purchased solution, 2M in THF, 22.5 mL) and the product of Example 14 step a) (5 g in 15 mL of THF, 18.1 mmol) were combined and warmed to 60° C. and stirred at 60° C. for 4 hours. The reaction mixture was allowed to cool to room temperature and the reaction vessel was placed in a cool water bath. Then triethanolamine (5.97 mL, 1 equiv.) was added at such a rate that the temperature of the reaction mixture was maintained between 20-25° C. Brine (17.5 mL) was added at a rate such that gas evolution was controlled and the mixture was stirred for 45 minutes at room temperature. The layers were separated, the organic layer was washed with brine (2×15 mL). The combined brine washes were extracted with MTBE (methyl tert-butyl ether, 3×20 mL). The combined organic extracts were evaporated and the residue was dissolved in MTBE (50 mL) and washed with brine (25 mL). The brine layer was back-extracted with MTBE (3×25 mL). The combined organic extracts were dried over Na$_2$SO$_4$, filtered, and concentrated to yield the desired diol (3.36 g, 15.5 mmol, 97%) as a colorless oil.

$^1$H NMR (CDCl$_3$) δ 1.22 (t, 6H), 1.73 (dd, 2H), 1.92 (m, 1H), 2.67 (bs, 2H), 3.52 (m, 2H), 3.69 (m, 2H), 3.72 (m, 4H), 4.62 (t, 1H).

c) Preparation of (2R)-2-acetoxymethyl-4,4-diethoxy-butanol

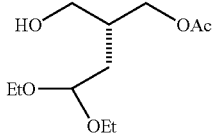

Into a 10 ml 1 neck round bottom flask was charged the product of Example 14 step b) (3.84 g, 20 mmol), followed by addition of vinyl acetate (2.6 g, 30 mmol) and finally Lipase PS 30 (69 mg, purchased from (Amano, Lombard, Ill.). The mixture was allowed to stir at ambient temperature for 16 hours. Progress of the reaction was closely monitored by TLC (2/1 hexane—EtOAc; stained with Ce$_2$(SO$_4$)$_3$ and charred on hot plate; r.f. of diol is 0.1, monoacetate is 0.3, bis acetate is 0.75). The reaction mixture was diluted with CH$_2$Cl$_2$ and filtered through a 5 micron filter. The filter was washed with additional CH$_2$Cl$_2$.

The filtrate was then concentrated in vacuo to afford the desired product.

d) Preparation of (2S)-2-acetoxymethyl-4,4-diethoxybutyl Toluenesulfonate

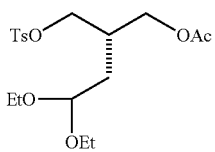

Into a 100 mL 1-neck round bottom flask, equipped with a magnetic stir bar and septum under N2 was charged the crude product of Example 14 step c) (4.62 g, 19 mmol), dry CH$_2$Cl$_2$ (20 mL) and Et$_3$N (5.62 mL, 40 mmol). To this solution was added tosyl chloride (4.76 g, 25 mmol). The resulting mixture was stirred at ambient temperature for 4 hours. Charged H$_2$O (0.27 g, 15 mmol) and stirred vigorously for 4 hours. The reaction mixture was diluted with 80 mL EtOAc and 50 mL H$_2$O and the aqueous layer was separated. To the organic layer was added 75 ml of a 5% aq. solution of KH$_2$PO$_4$. After mixing and separation of the layers, the aqueous layer was removed. The organic layer was washed with 50 mL of saturated NaHCO$_3$ solution, dried over Na$_2$SO$_4$, filtered and concentrated in vacuo to a constant weight of 7.40 g of the desired product.

$^1$H NMR (CDCl$_3$) δ 1.17 (t, 6H); 1.62 (m, 2H); 1.94 (s, 3H); 2.19 (m, 1H); 2.45 (s, 3H); 3.42 (m, 2H); 3.6 (m, 2H); 4.03 (m, 4H); 4.51 (t, 1H); 7.36 (d, 2H); 7.79 (d, 2H).

e) Preparation of

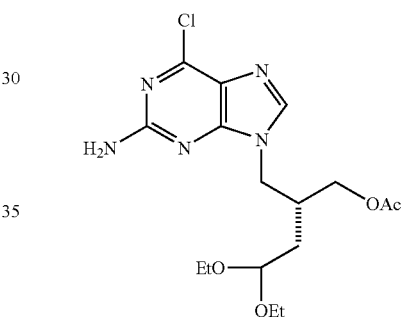

Into a 50 mL 1 neck round bottom flask was charged the product of Example 14 step d) (3.88 g, 10 mmol), anhydrous DMF (20 mL), 2-amino-4-chloro-purine (2.125 g, 12.5 mmol) and K$_2$CO$_3$ (4.83 g). The resulting suspension was stirred at 40° C. under a N$_2$ blanket for 20 hours. The mixture was concentrated to remove most of the DMF on a rotary evaporator. The residue was diluted with EtOAc (50 mL) and H$_2$O (50 mL). The reaction mixture was transferred to a separatory funnel, shaken and the aqueous layer was separated. The aqueous layer was extracted with EtOAc (25 mL). The organic layers were combined and washed with 5% KH$_2$PO$_4$ (75 mL). The organic layer was separated and washed with H$_2$O (75 mL), brine (75 mL), dried over Na$_2$SO$_4$, filtered and concentrated in vacuo to afford 3.95 g of crude product. The crude product was slurried with 40 mL of methyl-t-butyl ether. This mixture was stirred overnight at 4° C. and the mixture was filtered. The filtrate was concentrated to afford 3.35 g of the product as an oil (containing 2.6 g of the desired product based upon HPLC analysis).

300 MHz $^1$H NMR (CDCl$_3$) δ 1.19 (m, 6H); 1.69 (2H); 1.79 (s, 1H); 2.03 (s, 3H); 2.52 (m, 1H); 3.48 (m, 2H); 3.62 (m, 2H); 4.04 (m, 2H); 4.16 (m, 2H); 4.61 (t, 1H); 5.12 (bs, 2H); 7.81 (s, 1H).

f) Preparation of

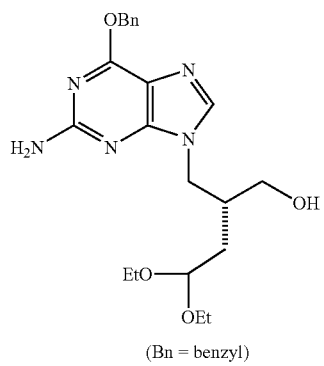

(Bn = benzyl)

Into a 500 mL 1 neck round bottom flask was charged benzyl alcohol (136 mL), cooled to 0° C., followed by portionwise addition of KO-t-Bu (36 g, 321 mmol). The temperature was allowed to warm to 40° C., and the mixture was stirred 20 minutes. To this mixture was added at 0° C. the crude product of Example 14 step e) (24.7 g, 64.2 mmol) dissolved in 25 mL anhydrous THF and benzyl alcohol (30 mL). The temperature was allowed to slowly warm to 8° C. over 2 hours. The reaction mixture was poured into 500 mL ice and was extracted with 500 mL MTBE. The organic layer was washed with 250 mL of brine, dried over $Na_2SO_4$, filtered and concentrated in vacuo to afford 193 g of a benzyl alcohol solution of the desired product. HPLC analysis indicated that the solution contained 25.96 g of the desired product.

300 MHz $^1$H NMR ($CDCl_3$) δ 1.22 (m,6H); 1.55 (2H); 2.18 (m, 1H); 3.15 (m, 1H); 3.40 (m, 1H); 3.51 (m, 2H); 3.70 (m, 2H); 4.25 (m, 2H); 4.63 (t,1H); 4.90 (bs, 2H); 5.25 (m, 1H); 5.58 (s, 2H); 7.35 (m, 3H); 7.51 (m, 2H); 7.72 (s, 1H). MS=(M+H)+=416 (CI).

g) Preparation of

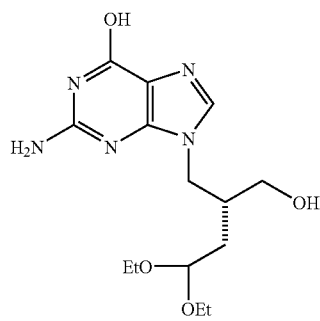

Into a 100 mL 1 neck round bottom flask was charged the crude product of Example 14 step f) (9.65 g of the benzyl alcohol solution, containing 1.30 g, 3.13 mmol of the product of Example 14, step f) dissolved in absolute EtOH (20 mL). To this was added 0.45 g of 10% Pd/C slurried in 5 mL absolute EtOH. The reaction flask was evacuated and charged with $H_2$ three times with a balloon of $H_2$. The reaction flask was pressurized with 1 atm. $H_2$ and the reaction mixture was stirred overnight. The reaction mixture was filtered through a pad of diatomaceous earth to remove Pd/C. The volatiles were removed in vacuo. The residue was mixed with 25 mL of isopropyl acetate and then concentrated in vacuo. The residue was diluted with EtOAc (10 mL), seeded with the desired product, heated to reflux and then $CH_3CN$ (2 mL) and MTBE (35 ml) were added. The mixture was stirred for 30 minutes. The precipitate was filtered and dried to a constant weight of 600 mg of the desired product.

300 MHz $^1$H NMR (d6-DMSO) δ 1.16 (m,6H); 1.45 (m, 1H); 1.61 (m, 1H); 2.16 (m, 1H); 3.45 (m, 2H); 3.40 (m, 1H); 3.62 (m, 2H); 4.02 (m,2H); 4.53 (t, 1H); 4.85 (t, 1H); 6.55 (bs, 1H); 7.75 (s, 1H). MS=(M+H)+=416 (CI).

h) Preparation of

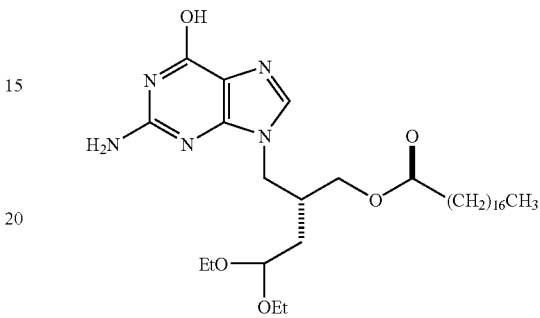

Into a 25 mL 1 neck round bottom flask was charged the product of Example 14 step g) (0.650 g, 2.0 mmol), pyridine (4 mL) and $CH_2Cl_2$ (2 mL), DMAP (10 mg). The mixture was cooled to −5° C. and stearoyl chloride (790 mg, 2.6 mmol) dissolved in $CH_2Cl_2$ (0.5 mL) was added over 5 minutes. The resulting mixture was stirred 16 hours at −5° C. Absolute EtOH (0.138 g, 3.0 mmol) was added and the mixture was stirred an additional 1 hour. The reaction mixture was concentrated in vacuo. Toluene (30 mL) was added to the residue and then the mixture was concentrated in vacuo. Again, toluene (30 mL) was added to the residue and then the mixture was concentrated in vacuo. To the residue was added 1% $KH_2PO_4$ (25 mL) and this mixture was extracted with $CH_2Cl_2$ (60 mL). The organic layer was separated and was dried over $Na_2SO_4$, filtered and concentrated in vacuo to a constant weight of 1.65 g. The crude product was chromatographed on 40 g of $SiO_2$, eluting with 95/5 $CH_2Cl_2$— EtOH, affording 367 mg of the desired product.

300 MHz $^1$H NMR ($CDCl_3$) δ 0.89 (t, 3H); 1.26 (m, 30H); 1.65 (m,3H); 2.32 (m, 1H); 3.45 (m, 1H); 3.60 (m, 2H); 4.08 (m, 2H); 4.60 (m, 1H); 6.0 (bs, 2H); 7.53 (s, 1H).

i) Preparation of

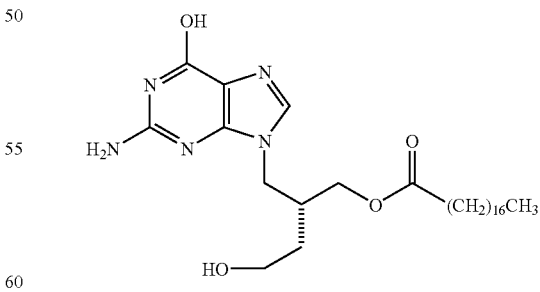

Into a 25 mL 1 neck round bottom flask was charged the product of Example 14, step h) (0.234 g, 0.394 mmol) dissolved in THF (1.7 mL). To this solution was added triflic acid (0.108 g) in $H_2O$ 180 mg. The mixture was stirred overnight at room temperature. To the reaction mixture was added saturated $NaHCO_3$ solution (10 mL), THF (5 mL), $CH_2Cl_2$ (2 mL)

and NaBH₄ (0.10 g). This mixture was stirred for 30 minutes. To the reaction mixture was added a 5% solution of KH₂PO₄ (30 mL). This mixture was extracted with 2×15 ml of CH₂Cl₂. The organic layers were combined and dried over Na₂SO₄, filtered and concentrated in vacuo to a constant weight of 207 mg. This material was recrystallized from EtOAc (8 mL) and CH₃CN (0.5 mL) affording 173 mg of the desired product.

300 MHz ¹H NMR (d6-DMSO) δ 0.82 (t, 3H); 1.19 (m, 30H); 1.41 (m, 4H); 2.19 (t, 2H); 2.32 (m, 1H); 3.40 (m, 2H); 3.9 (m, 4H); 4.49 (m, 1H); 6.4 (bs, 2H); 7.61 (m, 1.5H); 9.55 (m, 0.5H).

EXAMPLE 15

Alternative Preparation of (R)-9-[4-(N-tert-butyloxy-carbonyl-L-valyloxy)-2-(stearoyloxymethyl)butyl] guanine (R)-9-[2-(Stearoyloxymethyl)-4-(t-butyldiphenylsilyloxy)butyl]guanine (45 g) and THF (950 ml) were combined in a 2L flask. Then Boc-L-valine (3.22 g, 0.25 eq) was added, followed by tetrabutylammonium fluoride (1M in THF, 89.05 mL) over 10 minutes. The clear reaction mixture was stirred at room temperature for 2 hours and 50 minutes with monitoring of the reaction progress by TLC (90/10 CH₂Cl₂/MeOH).

To the reaction mixture was added Boc-L-valine (35.43 g, 2.75 eq), DCC (36.67 g, 2.75 eq) and dimethylaminopyridine (1.1 g, 0.15 eq) in THF (25 ml). The reaction mixture was stirred at room temperature for 24 hours. DCU was filtered off and washed with CH₂Cl₂. The filtrate was concentrated, and the residue was taken up in 2 litres of CH₂CL₂ and washed with 2L of ½ saturated sodium bicarbonate and brine solutions. On drying and evaporation, approximately 100 g of crude product was obtained. The material was purified by silica chromatography (6000 ml of silica) using 3% MeOH/CH₂Cl₂ to 5% MeOH/CH₂Cl₂ to obtain 38.22 mg of the desired product.

EXAMPLE 16

Alternative Preparation of (R)-9-[2-(stearoyloxymethyl)-4-(L-valyloxy)butyl]guanine a) (R)-9-[2-Hydroxymethyl)-4-(t-butyldiphenylsilyloxymethyl)butyl]guanine H2G (450.0 g, 1.78 mol) and N,N dimethylformamide (6.4 kg) were charged into a Bucchi evaporator and the mixture warmed to dissolve the solid. The solution was concentrated to dryness under vauum at no more than 90° C. The resulting powder was transferred to a 22 litre flask with stirrer, addition funnel and and temperature probe. N,N-dimethylformamide (1.7 kg) was added followed by pyridine (3.53 kg). The resulting suspension was cooled to −10° C. under nitrogen and stirred at −5±5° C. as t-butylchlorodiphenylsilane (684 g, 2.49 mol) was added dropwise. The resulting mixture was stirred at −5±5° C. until the reaction was complete (as monitored by TLC (10:1 methylene chloride/methanol) and HPLC (4.6×250 mm Zorbax RxC8 (5 micron); 60:40 acetonitrile-aq. NH₄OAC (0.05 M) at 1.5 ml/min; UV detection at 254 nm)). Water (16 kg) was added and the mixture was stirred for 30 minutes to precipitate the product, then the mixture was cooled to 0° C. for 30 minutes. The solid was isolated by filtration and the product cake was washed with cold water and sucked dry with air to provide the crude product as an off-white solid. The crude solid was taken up in pydridine (3 kg) and concentrated under vacuum at 60° C. to remove water. The dry solid residue was slurried with methanol (10 kg) at 60° C. for 1-2 hours and filtered while hot. The filtrate was concentrated under vacuum and the solid residue was refluxed with isopropyl acetate (7 kg) for 30 minutes. The mixture was cooled to 20° C. and filtered. The filter cake was dried under vacuum at 50° C. to provide the title compound as a white solid (555 g).

b) (R)-9-[2-(Stearoyloxymethyl)-4-(t-butyldiphenylsilyloxy)butyl]guanine

The product of Example 16, step a) (555 g, 1.113 mol) was charged to a 50 litre Buchi evaporator. Pyridine (2.7 kg) was added dropwise to dissolve the solid and the mixture was distilled to dryness under vacuum at 60° C. The residue was taken up in fresh pyridine (2.7 kg) and transferred to a 22 litre flask with stirrer, addition funnel and temperature probe. The solution was cooled to −5° C. under nitrogen. A solution of stearoyl chloride (440 g, 1.45 mol) in methylene chloride (1.5 kg) was added so as to maintain a temperature below 0° C. 4-(N,N-dimethylamino)pyridine (15 g, 0.12 mol) was added and the mixture was stirred at −5-0° C. for 2-4 hours until conversion was complete (as monitored by TLC (10:1 methylene chloride/methanol) and HPLC (4.6×250 mm Zorbax RxC8 (5 micron); 60:40 acetonitrile-aq. NH₄OAc (0.05 M) at 1.5 ml/min; UV detection at 254 nm)). At the end of the reaction, acetonitrile (8.7 kg) was added and the mixture was stirred for not less than 15 minutes to precipitate the product. The slurry was cooled to 0° C. for 2 hours and the solid isolated by filtration and the filter cake washed with acetonitrile (2 kg). The desired product was obtained as a white solid (775 g).

c) (R)-9-[4-Hydroxy-2-(stearoyloxymethyl)butyl]guanine

A solution of the product of Example 16, step b) (765 g, 0.29 mol) in tetrahydrofuran (10 kg) was prepared in a reactor. A solution of tetra(n-butyl)ammonium fluoride in tetrahydrofuran (1.7 kg of 1 M solution, 1.7 mol) was added and the resulting clear solution was stirred at 20±5° C. for 4 hours. Water (32 kg) was added and the resulting slurry was stirred for 1 hour and then cooled to 0° C. for 30 minutes. The precipitate was isolated by filtration and the filter cake was washed successively with water (10 kg) and acetonitrile (5 kg). After drying under vacuum at 25° C., 702 g of crude product was obtained. The crude product was dissolved in refluxing THF (4.2 kg) and water (160 g), then cooled to 40° C. and treated with methylene chloride (14.5 kg). The mixture was allowed to cool to 25±5° C. for 1 hour, then it was cooled to 5±5° C. for 1 hour to complete precipitation. The slightly off-white powder was isolated by filtration and dried under vacuum at 40° C. to yield the desired product (416 g).

d) (R)-9-[4-(N-Cbz-L-valyloxy)-2-(stearoyloxymethyl)butyl]guanine

A solution of N-Cbz-L-valine (169 g, 0.67 mol) in dry THF (750 ml) was prepared in a 2 litre flask with mechanical stirrer, thermometer and addition funnel. A solution of dicyclohexylcarbodiimide (69.3 g, 0.34 mol) in THF (250 ml) was added over 5 minutes and the resulting slurry was stirred at 20±5° C. for 2 hours. The slurry was filtered and the filter cake was washed with THF (300 ml). The filtrate and wash were charged to a 3 litre flask with stirrer and thermometer. The product of Example 16, step c) (116 g, 0.22 mol) was added as a solid, with a rinse of THF (250 ml). 4-(N,N-dimethylamino) pyridine (2.73 g, 0.022 mol) was added and the white slurry stirred at 20±5° C. Within 15 minutes, the solids were all dissolved and the reaction was complete within 1 hour (as determined by HPLC: 4.6×250 mm Zorbax RxC8 column;

85:15 acetonitrile-0.2% aq. HClO$_4$ at 1 ml/min.; UV detection at 254 nm; starting material elutes at 4.1 min. and product elutes at 5.9 min.). The reaction was quenched by addition of water (5 ml) and the solution was concentrated under vacuum to leave a light yellow semisolid. This was taken up in methanol (1.5 litres) and warmed to reflux for 30 minutes. The solution was cooled to 25° C. and the precipitate was removed by filtration. The filtrate was concentrated under vacuum to leave a viscous, pale yellow oil. Acetonitrile, (1 L) was added and the resulting white suspension was stirred at 20±5° C. for 90 minutes. The crude solid product was isolated by filtration, washed with acetonitrile (2×100 ml) and air-dried overnight to provide the desired product as a waxy, sticky solid (122 g). This was further purified by crystallization from ethyl acetate (500 ml) and drying under vacuum at 30° C. to provide the desired product as a white, waxy solid (104 g).

e) (R)-9-[4-(L-valyloxy)-2-(stearoyloxymethyl)butyl]guanine

A solution of the product of Example 16, step d), (77 g) in warm (40° C.) ethanol (2.3 L) was charged to an hydrogenation reactor with 5% Pd-C (15.4 g). The mixture was agitated at 40° C. under 40 psi hydrogen for 4 hours, evacuated and hydrogenated for an additional 4-10 hours. The catalyst was removed by filtration and the filtrate was concentrated under vacuum to provide a white solid. This was stirred with ethanol (385 ml) at 25° C. for 1 hour, then cooled to 0° C. and filtered. The filter cake was dried with air, then under vacuum at 35° C. to yield the title compound as a white powder (46 g).

EXAMPLE 17

(R)-9-[2-(L-Valyloxymethyl)-4-(stearoyloxy)butyl] guanine a) (R)-9-[2-Hydroxymethyl-4-(stearoyloxy)butyl]guanine.

H2G (506 mg; 2.0 mmol) was dissolved in dry N,N-dimethylformamide (40 ml) with pyridine (400 mg; 5.06 mmol) and 4-dimethylaminopyridine (60 mg; 0.49 mmol). Stearoyl chloride (1500 mg; 4.95 mmol) was added and the mixture kept overnight at room temperature. Most of the solvent was evaporated in vacuo, the residue stirred with 70 ml ethyl acetate and 70 ml water, and the solid filtered off, washed with ethyl acetate and water and dried to yield 680 mg of crude product.

Column chromatography on silica gel (chloroform:methanol 15:1) gave pure title compound as a white solid.

$^1$H NMR (DMSO-d$_6$) δ: 0.86 (t, 3H); 1.25 (s, 28H); 1.51 (qui, 2H); 1.62 (m, 2H); 2.06 (m, 1H); 2.23 (t, 2H); 3.34 (d, 2H); 3.96 (ABX, 2H); 4.07 (dd, 2H); 6.30 (br s, 2H); 7.62 (s, 1H); 10.45 (s, 1H).

$^{13}$C NMR (DMSO-d$_6$) δ: 13,8 (C18); 22.0 (C17); 24.4 (C3); 27.7 (C3'); 28.4-28.8 (C$_{4-6}$, C15); 28.9 (C$_{7-14}$); 31.2 (C16); 33.5 (C2); 38.0 (C2'); 44.0 (C1'); 60.6/61.8 (C4', C2''); 116.5 (guaC5); 137.7 (guaC7); 151.4 (guaC4); 153.5 (guaC2); 156.7 (guaC6); 172.7 (COO).

b) (R)-9-[2-(N-Boc-L-valyloxymethyl)-4-(stearoyloxy)butyl]guanine.

A mixture of N-Boc-L-valine (528 mg; 2.1 mmol) and N,N'-dicyclohexyl carbodiimide (250 mg; 1.21 mg) in dichloromethane (20 ml) was stirred over night at room temperature, dicyclohexylurea filtered off and extracted with a small volume of dichloromethane, and the filtrate evaporated in vacuo to a small volume. (R)-9-[2-Hydroxymethyl-4-(stearoyloxy)butyl]guanine (340 mg; 0.654 mmol), 4-dimethylaminopyridine (25 mg; 0.205 mmol), and dry N,N-dimethylformamide (15 ml) were added and the mixture was stirred for 4 h at 50° C. under N$_2$. The solvent was evaporated in vacuo to a small volume. Column chromatography on silica gel, then on aluminum oxide (ethyl acetate:methanol: water 15:2:1 as eluent) gave 185 mg (39%) pure title compound as a white solid.

$^1$H NMR (CHCl$_3$) δ: 0.85-1.0 (m, 9H) 18-CH$_3$, CH(CH$_3$)$_2$; 1.25 (s, 28H) 4-17-CH$_2$; 1.44 (s, 9H) t-Bu; 1.60 (qui, 2H) 3-CH$_2$; 1.74 (qua, 2H) 3'-CH$_2$; 2.14 (m, 1H) 2'-CH; 2.29 (t, 2H) 2-CH$_2$; 2.41 (m,1H)CH(CH$_3$)$_2$; 4.1-4.3 (m, 6H)C1'-CH$_2$, C2''-CH$_2$, C4-CH$_2$; 5.4 (d, 1H) αCH; 6.6 (br s, 2H) guaNH$_2$; 7.73 (s, 1H) guaH8; 12.4 (br s).

$^{13}$C NMR (CHCl$_3$) δ: 13,9 (C18); 17.5/18.9 (2 Val CH$_3$); 22.4 (C17); 24.7 (C3); 28.1 (C3'); 28.9-29.3 (C$_{4-6}$, C15); 29.4 (C$_{7-14}$); 30.7 (Val βC); 31.7 (C16); 34.0 (C2); 35.9 (C2'); 43.9 (C1'); 58.7 (Val αC); 61.4/63.6 (C4', C2''); 79.9 (CMe$_3$); 116.4 (guaC5); 137.9 (guaC7); 151.7 (guaC4); 153.7 (guaC2); 155.7 (CONH); 158.8 (guaC6); 172.1 (CHCOO); 173.5 (CH$_2$COO).

c) (R)-9-[2-(L-Valyloxymethyl)-4-(stearoyloxy)butyl]guanine.

Chilled trifluoroacetic acid (2.0 g) was added to (R)-9-[2-(N-Boc-L-valyloxymethyl)-4-(stearoyloxy)butyl]guanine (180 mg; 0.25 mmol) and the solution kept at room temperature for 1 h, evaporated to a small volume, and lyophilized repeatedly with dioxane until a white amorphous powder was obtained. The yield of title compound, obtained as the trifluoracetate salt, was quantitative.

$^1$H NMR (DMSO-d$_6$) δ: 0.87 (t, 3H) 18-CH$_3$, 0.98 (dd, 6H)CH(CH$_3$)$_2$; 1.25 (s, 28H) 4-17-CH$_2$; 1.50 (qui, 2H) 3-CH$_2$; 1.68 (qua, 2H) 3'-CH$_2$; 2.19 (m, 1H) 2'-CH; 2.26 (t, 2H) 2-CH$_2$; 2.40 (m,1H)CH(CH$_3$)$_2$; 3.9-4.25 (m, 7H)C1'-CH$_2$, C2''-CH$_2$, C4-CH$_2$, αCH; 6.5 (br s, 2H) guaNH$_2$; 7.79 (s, 1H) guaH8; 8.37 (br s, 3H) NH$_3$$^+$; 10.73 (br s, 1H) guaNH.

$^{13}$C NMR (DMSO-d$_6$) δ: 14.2 (C18); 17.9/18.3 (2 Val CH$_3$); 22.3 (C17); 24.6 (C3); 27.7 (C3'); 28.7-29.1 (C$_{4-6}$, C15); 29.2 (C$_{7-14}$); 29.5 (Val PC); 31.5 (C16); 33.7 (C2); 35.0 (C2'); 44.1 (C1'); 57.6 (Val αC); 61.6/65.2 (C4', C2''); 116.1 (guaC5);116.3 (qua, J290 Hz, CF$_3$);137.9 (guaC7); 151.5 (guaC4); 154.0 (guaC2); 156.7 (guaC6);158.3 (qua, J 15 Hz, CF$_3$COO) 169.1 (CHCOO); 173.1 (CH$_2$COO).

EXAMPLE 18

Alternative Preparation of (R)-9-[2-hydroxymethyl-4-(stearoyloxy)butyl]guanine

H2G (7.60 g, 30 mmol) was heated to solution in dry DMF (200 ml). The solution was filtered to remove solid impurities, cooled to 20° C. (H2G cystallized) and stirred at that temperature during addition of pyridine (9.0 g, 114 mmol), 4-dimethylaminopyridine (0.46 g, 3.75 mmol) and then, slowly, stearoyl chloride (20.0 g, 66 mmol). Stirring was continued at room temperature overnight. Most of the solvent was then evaporated off in vacuo, the residue stirred with 200 ml ethyl acetate and 200 ml water and the solid filtered off, washed with ethyl acetate and water and dried to yield crude product. As an alternative to recrystallization, the crude product was briefly heated to almost boiling with 100 ml of ethyl acetate: methanol: water (15:2:1) and the suspension slowly cooled to 30° C. and filtered to leave most of the 2'' isomer in solution (the 2'' isomer would crystallize at lower temperature). The extraction procedure was repeated once more to yield, after drying in vacuo, 6.57 g (42%) of almost isomer free product.

EXAMPLE 19

Preparation of Crystalline (R)-9-[2-stearoyloxymethyl)-4-(L-valyloxy)butyl]guanine The product of Example 16, step c) (20.07 g, 32.5 mmol) was dissolved in absolute ethanol (400 ml) with heating, filtered, and further diluted with ethanol (117.5 ml). To this solution was added water (HPLC grade, 103.5 ml), and the mixture was allowed to cool to 35-40° C. After the mixture was cooled, water (HPLC grade, 931.5 ml) was added at a constant rate over 16 hours with efficient stirring. After all the water was added, stirring was continued for 4 hours at room temperature. The resulting precipitate was filtered through paper and dried under vacuum at room temperature to obtain the title compound as a white, free flowing crystalline powder (19.43 g, 97%), m pt 169-170° C.

EXAMPLE 20

9-R-(4-Hydroxy-2-(L-valyloxymethyl)butyl)guanine a) To a solution of 9-R-(4-(tert-butyldiphenylsilyloxy)-2-(hydroxymethyl)butyl)guanine (695 mg, 1.5 mmole) in DMF (30 ml) were added N-Boc-L-Valine (488 mg, 2.25 mmole), 4-dimethylamino pyridine (30 mg, 0.25 mmole) and DCC (556 mg, 2.7 mmole). After 16 hr, the reaction was recharged with N-Boc-L-valine (244 mg) and DCC (278 mg), and was kept for an additional 5 hours. The reaction mixture was filtered through Celite and poured into sodium hydrogen carbonate aqueous solution, and then it was extracted with dichloromethane. The organic phase was evaporated and purified by silica gel column chromatography, giving 950 mg the N-protected monoamino acyl intermediate.

b) The above intermediate (520 mg, 0.78 mmole) was dissolved in THF (15 ml). To the solution was added hydrogen fluoride in pyridine (70%/30%, 0.34 ml). After two days, the solution was evaporated and coevaporated with toluene. Purification by silica gel column chromatography gave 311 mg of the protected monoamino acyl compound.

$^1$H-NMR (DMSO-$d_6$): δ 10.41(s, 1H), 7.59 (1H), 6.26 (br s, 2H), 4.32 (t, 1H), 3.95 (m, 5H), 3.46 (m, 2H), 2.41 (m, 1H), 2.06 (m, 1H), 1.45 (m, 2H), 1.39 (s, 9H), 0.90 (d, 6H).

c) The product of step b) (95 mg, 0.21 mmole) was treated with a mixture of trifluoroacetic acid (4 ml) and dichloromethane (6 ml) for 1 hr. The solution was evaporated and freeze-dried, give 125 mg of the unprotected monoaminoacyl product.

$^1$H-NMR ($D_2O$): δ 8.88 (s, 1H), 4.32 (m, 4H), 3.96 (d, 1H), 3.68 (m, 2H), 2.63 (m, 1H), 2.22 (m, 1H), 1.73 (m, 2H), 1.00 (m, 6H).

EXAMPLE 21

(R)-9-(2-Hydroxymethyl-4-(L-isoleucyloxy)butyl)guanine a) To a solution of (R)-9-(2-hydroxymethyl-4-hydroxybutyl)guanine (2.53 g, 10 mmole) in DMF (250 ml) were added N-Boc-L-isoleucine(2.77 g, 12 mmole), 4-dimethylaminopyridine (61 mg, 0.6 mmole) and DCC (3.7 g, 18 mmole). After reaction for 16 hr at 0° C., N-Boc-L-isoleucine (1.3 g) and DCC (1.8 g) were recharged, and the reaction was kept overnight at room temperature. The reaction mixture was filtered through Celite and the filtrate was evaporated and purified by silica gel column chromatography, giving 1.25 g of the N-protected monoamino acyl intermediate.

$^1$H-NMR (DMSO-$d_6$): δ 10.56 (s, 1H), 7.62 (s, 1H), 6.43 (s, 2H), 4.75 (t, 1H), 4.15-3.80 (m, 5H), 3.25 (m, 2H) 2.05 (m, 1H), 1.80-1-05 (m, 14H), 0.88 (m, 6H).

b) The intermediate from step a) (100 mg, 0.21 mmole) was treated with trifluoroacetic acid (3 m) and for 30 min at 0° C. The solution was evaporated and freeaze-dried, give the titled unprotected mono-aminoacyl product in quantitative yield.

$^1$H-NMR (DMSO-$d_6$+$D_2O$): δ 8.72 (s, 1H), 4.15 (m, 4H), 3.90 (d, 1H), 3.42 (m, 2H), 2.09 (m, 1H), 1.83 (m, 1H), 1.61 (m, 2H), 1.15 (m, H), 0.77 (d, 3H), 0.71 (t, 3H).

EXAMPLE 22

(R)-9-[2-Hydroxymethyl-4-(L-valyloxy)butyl]guanine

The product of Example 1, step a) was deprotected with trifluoroaacetic acid in the same manner as Example 1, step c)

$^1$H-NMR (250 MHz, DMSO-$d_6$): δ 1.04 (dd, 6H), 1.55-1.88 (m, 2H), 2.21 (m, 2H), 3.48 (m, 2H), 4.00 (m, 1H), 4.13 (m, 2H), 4.34 (t, 2H), 6.9 (br s, 2H), 8.21 (s, 1H), 8.5 (br s, 3H), 11.1 (br s, 1H).

EXAMPLE 23

(R)-9-[2-(L-Valyloxymethyl)-4-(valyloxy)butyl]guanine a) (R)-9-[4-(N-Boc-L-valyloxy)-2-(N-Boc-L-valyloxymethyl)butyl]guanine Application of the technique described in Example 1, step a), but using 2.7 eqs, 0.28 eqs, and 3.2 eqs of N-Boc-L-valine, DMAP, and DCC, respectively, resulted in the title compound.

$^1$H NMR (250 MHz, CHCl$_3$) δ: 0.95 (m, 12H), 1.42 (br s, 18H), 1.8 (m, 2H), 2.14 (m, 2H), 2.47 (m, 1H), 4.0-4.4 (m, 8H), 6.5 (br s, 2H), 7.67 (s, 1H).

b) (R)-9-[4-(L-Valyloxy)-2-(L-valyloxymethyl)butyl]guanine

The titled compound was obtained as the tris-trifluoroacetate salt from the intermediate of Example 20 step a) by deprotection in a manner analogous to Example 1 step c).

$^1$H NMR (250 MHz, $D_2O$) δ: 1.0 (m, 12H), 1.89 (m, 2H), 2.29 (m, 2H), 2.62 (m, 1H), 4.02 (dd, 2H), 4.38 (m, 6H), 4.89 (br s, ca. 10H), 8.98 (s, 1H).

EXAMPLE 24

(R)-9-[4-hydroxy-2-(stearoyloxymethyl)butyl]guanine

The titled compound is prepared according to steps a) to c) of Example 7.

$^1$H NMR (250 MHz, DMSO-$d_6$): δ 10.52 (s, 1H), 7.62 (s, 1H), 6.39 (s, 2H), 4.50 (t, 1H), 3.93 (m, 4H), 3.42 (m, 2H), 2.45 (m, 1H), 2.23 (t, 2H), 1.48 (m, 4H), 1.22 (s, 28H), 0.89 (t, 3H)

EXAMPLE 25

(R)-9-[2-Hydroxymethyl-4-(stearoyloxy)butyl]guanine.

The titled compound is prepared by the procedure of Example 17, step a)

¹H NMR (DMSO-d₆) δ: 0.86 (t, 3H); 1.25 (s, 28H); 1.51 (qui, 2H); 1.62 (m, 2H); 2.06 (m, 1H); 2.23 (t, 2H); 3.34 (d, 2H); 3.96 (ABX, 2H); 4.07 (dd, 2H); 6.30 (br s, 2H); 7.62 (s, 1H); 10.45 (s, 1H).

EXAMPLE 26

Alternative Preparation of (R)-9-[2-stearoyloxymethyl]-4-(L-valyloxy)butyl]guanine a) (R)-9-[4-N-benzyloxycarbonyl-L-valyloxy)-2-(hydroxymethyl)-butyl]guanine Dry H2G (252 mg, 1 mmol), 4-dimethylaminopyridine (122 mg, 1 mmol) and N-Cbz-L-valine p-nitrophenyl ester (408 mg, 1.1 mmol) were dissolved in dry dimethyl formamide (16 ml). After stirring at 23° C. for 30 hours, the organic solvent was removed and the residue carefully chromatographed (silica, 2%-7% methanol/methylene chloride) to afford the desired product as a white solid (151 mg, 31%).

b) (R)-9-[4-N-benzyloxycarbonyl-L-valyloxy)-2-(stearoyloxymethyl)-butyl]guanine

A solution of stearoyl chloride (394 mg, 1.3 mmol) in dry methylene chloride (2 ml) was added slowly dropwise under nitrogen to a solution of the product of step a) (243 mg, 1 mmol) and 4-dimethylaminopyridine (20 mg) in dry pyridine (5 ml) at −5° C. The reaction mixture was stirred at that temperature for 12 hours. Methanol (5 ml) was added and the reaction stirred for 1 hour. After removal of the solvent, the residue was triturated with acetonitrile and chromatographed (silica, 0-5% methanol/methylene chloride) to afford the desired product (542 mg, 72%).

c) (R)-9-[2-stearoyloxymethyl)-4-(L-valyloxy)butyl]guanine

The product of step b) (490 mg, 1 mmol) was dissolved in methanol (30 ml) and 5% Pd/C (100 mg) added. A balloon filled with hydrogen was placed on top of the reaction vessel. After 6 hours at 23° C., TLC showed the absence of starting material. The reaction mixture was filtered through a 0.45 micron nylon membrane to remove the catalyst and the solvent was removed to afford the desired product as a white solid (350 mg, 99%) which was identical (spectral and analytical data) to Example 16.

EXAMPLE 27

Alternative Preparation of (R)-9-(4-hydroxy-2-(L-valyloxymethyl)butyl)guanine (R)-9-(4-(L-valyloxy)-2-(L-valyloxymethyl) butyl)guanine from Example 23 step b) (100 mg, 0,126 mmole) was dissolved in 0.1 N NaOH aqueous solution (6.3 ml, 0.63 mmole) at room temperature. At intervals, an aliquot was taken and neutralized with 0.5 N trifluoroacetic acid. The aliquots were evaporated and analyzed by HPLC to monitor the progress of the reaction. After 4 hours, 0.5 N trifluoroacetic acid solution (1.26 ml, 0.63 mmole) was added to the solution and the reaction mixture was evaporated. The desired product was purified by HPLC, (YMC, 50×4.6 mm, gradient 0.1% TFA+0-50% 0.1% TFA in acetonitrile, in 20 minutes, UV detection at 254 nm. Yield: 13.6%

¹H-NMR (D₂O): δ 8.81 (s, 1H), 4.36 (m, 4H), 4.01 (d, 1H), 3.74 (m, 2H), 2.64 (m, 1H), 2.25 (m, 1H), 1.73 (m, 2H), 1.03 (dd, 6H).

EXAMPLE 28

Alternative Preparation of (R)-9-(2-hydroxymethyl-4-(L-valyloxy)butyl)guanine

HPLC separation of the reaction solution from Example 27 gave the titled compound in 29.2% yield.

¹H-NMR (DMSO-d₆): δ 8.38 (s, 3H), 8.26 (s, 1H), 6.83 (br s, 2H), 4.23 (m, 2H), 4.06 (m, 2H), 3.91 (m, 1H), 3.40 (m, 2H), 2.19 (m, 2H), 1.8-1.40 (m, 2H), 0.95 (dd, 6H).

EXAMPLE 29

(R)-9-[2-stearoyloxymethyl]-4-(L-valyloxy)]butyluanine Monohydrochloride

The product of Example 16, step d) (360 mg, 0.479 mmol) was dissolved in a mixture of methanol (10 ml) and ethyl acetate (10 ml). To the solution was added 10% Pd/C (100 mg) and 1N HCl (52.0 microlitres). The reaction mixture was stirred at room temperature for 2 hours under 1 atm. H2. The reaction mixture was filtered and the solvent evaporated from the filtrate to provide the desired product as a crystalline solid (300 mg).

FORMULATION EXAMPLE A

Tablet Formulation

The following ingredients are screened through a 0.15 mm sieve and dry-mixed

| | |
|---|---|
| 10 g | (R)-9-[2-(stearoyloxymethyl)-4-(L-valyloxy)butyl]guanine |
| 40 g | lactose |
| 49 g | crystalline cellulose |
| 1 g | magnesium stearate |

A tabletting machine is used to compress the mixture to tablets containing 250 mg of active ingredient.

FORMULATION EXAMPLE B

Enteric Coated Tablet

The tablets of Formulation Example A are spray coated in a tablet coater with a solution comprising

| | |
|---|---|
| 120 g | ethyl cellulose |
| 30 g | propylene glycol |
| 10 g | sorbitan monooleate |
| ad 1 000 ml | aq. dist. |

FORMULATION EXAMPLE C

Controlled release formulation

| | |
|---|---|
| 50 g | (R)-9-[2-(stearoyloxymethyl)-4-(L-valyloxy)butyl]guanine |
| 12 g | hydroxypropylmethylcellulose (Methocell K15) |
| 4.5 g | lactose | are dry-mixed and granulated with an aqueous paste of povidone. Magnesium stearate (0.5 g) is added and the mixture compressed in a tabletting machine to 13 mm diameter tablets containing 500 mg active agent.

FORMULATION EXAMPLE D

Soft Capsules

| | |
|---|---|
| 250 g | (R)-9-[2-(stearoyloxymethyl)-4-(L-valyloxy)butyl]guanine |
| 100 g | lecithin |
| 100 g | arachis oil |

The compound of the invention is dispersed in the lecithin and arachis oil and filled into soft gelatin capsules.

BIOLOGY EXAMPLE 1

Bioavailability Testing in Rats

The bioavailability of compounds of the invention were compared to the parent compound H2G and other H2G derivatives in a rat model. Compounds of the invention and comparative compounds were administered, per oral (by catheter into the stomach), to multiples of three individually weighed animals to give 0.1 mmol/kg of the dissolved prodrug in an aqueous (Example 4, 5, Comparative example 1-3, 5, 8), peanut oil (Comparative examples 4, 9, 10) or propylene glycol (Example 1-3, 6-12, 17, Comparative example 6, 7) vehicle dependent on the solubility of the test compound ingredient. The animals were fasted from 5 hours before to approximately 17 hours after administration and were maintained in metabolic cages. Urine was collected for the 24 hours following administration and frozen until analysis. H2G was analysed in the urine using the HPLCIUV assay of Ståhle & Öberg, Antimicrob Agents Chemother. 36 No 2, 339-342 (1992), modified as follows: samples upon thawing are diluted 1:100 in aq dist $H_2O$ and filtered through an amicon filter with centrifugation at 3000 rpm for 10 minutes. Duplicate 30 µl samples are chromatographed on an HPLC column; Zorbax SB-C18; 75×4.6 mm; 3.5 micron; Mobile phase 0.05M $NH_4PO_4$, 3-4% methanol, pH 3.3-3.5; 0.5 ml/min; 254 nm, retention time for H26 at MeOH 4% and pH 3.33, ~12.5 min. Bioavailability is calculated as the measured H2G recovery from each animal averaged over at least three animals and expressed as a percentage of the averaged 24 hour urinary H2G recovery from a group of 4 individually weighed rats respectively injected i.v.jugularis with 0.1 mmol/kg H2G in a Ringer's buffer vehicle and analysed as above.

Comparative example 1 (H2G) was from the same batch as used for preparation of Examples 1 to 12. The preparation of Comparative example 2 (monoVal-H2G) and 3 (diVal-H2G) are shown in Examples 21 and 23. Comparative example 4 (distearoyl H2G) was prepared by di-esterification of unprotected H2G in comparable esterification conditions to step 2 of Example 1. Comparative examples 5 & 8 (Val/Ac H2G) were prepared analogously to Example 4 using acetic anhydride with relevant monovaline H2G. Comparative example 6 (Ala/stearoyl H2G) was prepared analogously to Example 6 using N-t-Boc-L-alanine in step 4. Comparative example 7 (Gly/decanoyl) was prepared analogously to Example 5 but using the step 1 intermediate made with N-t-Boc-L-glycine. The preparation of Comparative examples 9 and 10 is shown in Examples 24 and 25 respectively. The results appear on Table 2 overleaf:

TABLE 2

| Compound | $R_1$ | $R_2$ | Bioavailability |
|---|---|---|---|
| Comparative example 1 | hydrogen | hydrogen | 8% |
| Comparative example 2 | valyl | hydrogen | 29% |
| Comparative example 3 | valyl | valyl | 36% |
| Example 1 | valyl | stearoyl | 56% |
| Comparative example 4 | stearoyl | stearoyl | 1% |
| Example 2 | valyl | myristoyl | 57% |
| Example 3 | valyl | oleoyl | 51% |
| Example 4 | valyl | butyryl | 45% |
| Comparative example 5 | valyl | acetyl | 11% |
| Example 5 | valyl | decanoyl | 48% |
| Example 6 | valyl | docosanoyl | 48% |
| Example 7 | isoleucyl | stearoyl | 53% |
| Example 8 | isoleucyl | decanoyl | 57% |
| Example 9 | isoleucyl | myristoyl | 49% |
| Example 10 | valyl | 4-acetylbutyryl | 52% |
| Example 11 | valyl | dodecanoyl | 46% |
| Example 12 | valyl | palmitoyl | 58% |
| Example 17 | stearoyl | valyl | 52% |
| Comparative example 6 | alanyl | stearoyl | 23% |
| Comparative example 7 | glycyl | decanoyl | 25% |
| Comparative Example 8 | acetyl | valyl | 7% |
| Comparative Example 9 | hydrogen | stearoyl | 12% |
| Comparative Example 10 | stearoyl | hydrogen | 7% |

Comparison of the bioavailabilities of the compounds of the invention with the comparative examples indicates that the particular combination of the fatty acids at $R_1/R_2$ with the amino acids at $R_1/R_2$ produces bioavailabilities significantly greater than the corresponding diamino acid ester or difatty acid ester. For example, in this model, the compound of Example 1 displays 55% better bioavailability than the corresponding divaline ester of Comparative example 3. The compound of Example 4 displays 25% better availability than the corresponding divaline ester.

It is also apparent, for instance from Comparative examples 5, 6 and 7 that only the specified fatty acids of this invention in combination with the specified amino acids produce these dramatic and unexpected increases in pharmacokinetic parameters.

BIOLOGY EXAMPLE 2

Plasma Concentrations in Rats

A plasma concentration assay was done in male Sprague Dawley derived rats. The animals were fasted overnight prior to dosing but were permitted free access to water. Each of the compounds evaluated was prepared as a solution/suspension in propylene glycol at a concentration corresponding to 10 mg H2G/ml and shaken at room temperature for eight hours. Groups of rats (at least 4 rats in each group) received a 10 mg/kg (1 ml/kg) oral dose of each of the compounds; the dose was administered by gavage. At selected time points after dosing (0.25, 0.5, 1, 1.5, 2, 4, 6, 9, 12, 15, and 24 hours after dosing), heparinized blood samples (0.4 ml/sample) were obtained from a tail vein of each animal. The blood samples were immediately chilled in an ice bath. Within two hours of collection, the plasma was separated from the red cells by centrifugation and frozen till analysis. The components of interest were separated from the plasma proteins using acetonitrile precipitation. Following lyophilisation, and reconstitution, the plasma concentrations were determined by reverse phase HPLC with fluorescence detection. The oral uptake of H2G and other test compounds was determined by comparison of the H2G area under the curve derived from the oral dose compared to that obtained from a 10 mg/kg intravenous dose of H2G, administered to a separate group of rats. The results are depicted in Table 1B above.

BIOLOGY EXAMPLE 3

Bioavailability in Monkeys.

The compounds of Example 1 and Comparative example 3 (see Biology Example 1 above) were administered p.o. by gavage to cynomolgus monkeys. The solutions comprised:

| Example 1 | 150 mg dissolved in 6.0 ml propylene glycol, corresponding to 25 mg/kg or 0.0295 mmol/kg. |
| Comparative Example 3 | 164 mg dissolved in 7.0 ml water, corresponding to 23.4 mg/kg or 0.0295 mmol/kg. |

Blood samples were taken at 30 min, 1, 2, 3, 4, 6, 10 and 24 hours. Plasma was separated by centrifugation at 2500 rpm and the samples were inactivated at 54° C. for 20 minutes before being frozen pending analysis. Plasma H2G levels were monitored by the HPLC/UV assay of Example 30 above.

FIG. 1 depicts the plasma H2G recovery as a function of time. Although it is not possible to draw statistically significant conclusions from single animal trials, it appears that the animal receiving the compound of the invention experienced a somewhat more rapid and somewhat greater exposure to H2G than the animal which received an alternative prodrug of H2G.

BIOLOGY EXAMPLE 4

Antiviral Activity

Figure 2:
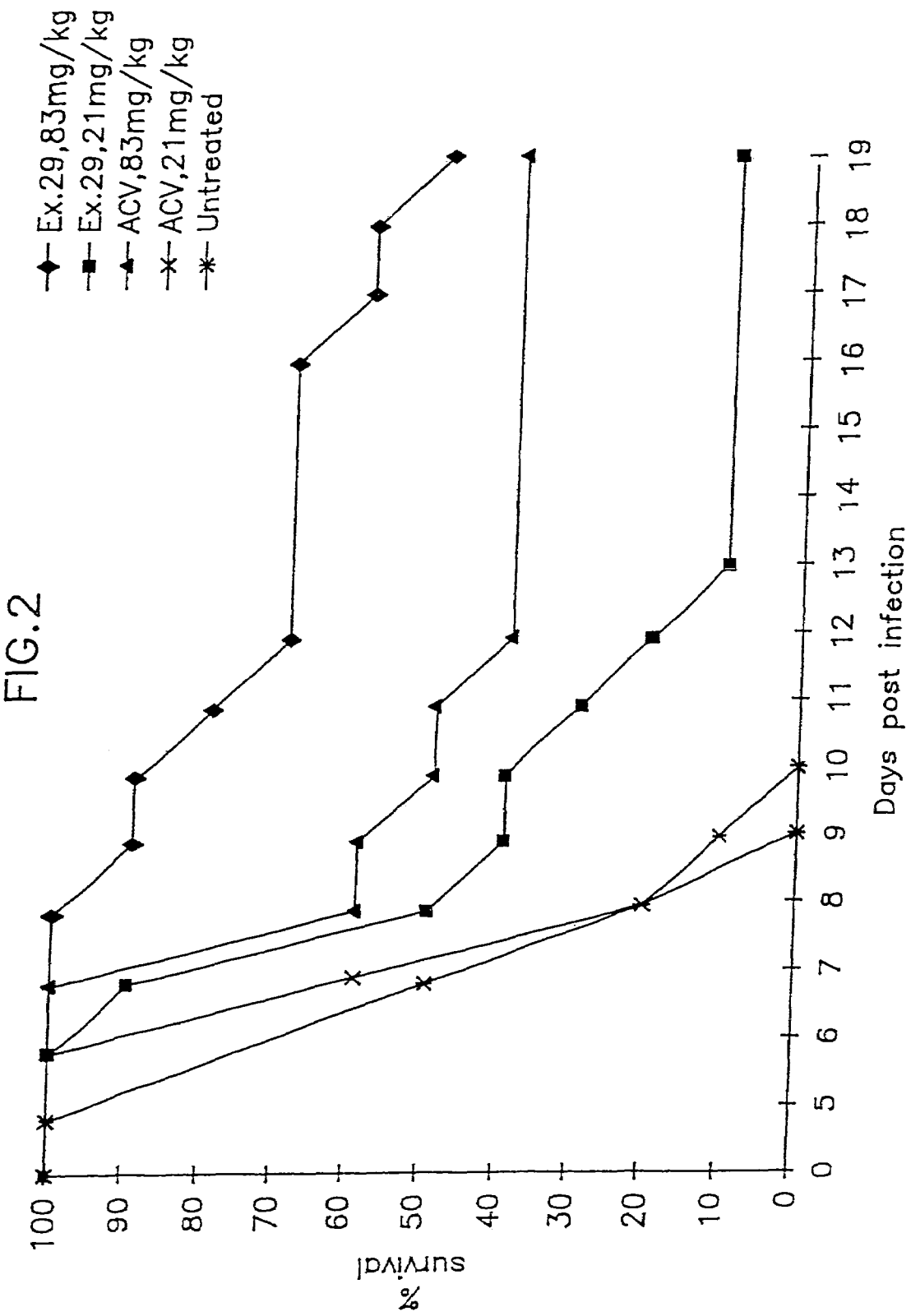
FIG. 2 depicts survival as a function of time for Herpes simplex infected mice administered with various doses of a compound of the invention or a prior art antiviral, as further explained in Biological Example 4.

Herpes simplex virus-1 (HSV-1)-infected mouse serves as an animal model to determine the efficacy of antiviral agents in vivo. Mice inoculated intraperitoneally with HSV-1 at 1000 times the $LD_{50}$ were administered either with a formulation comprising the currently marketed anti-herpes agent acyclovir (21 and 83 mg/kg in a 2% propylene glycol in sterile water vehicle, three times daily, p.o.) or the compound of Example 29 (21 and 83 mg/kg in a 2% propylene glycol in sterile water vehicle, three times daily, p.o.) for 5 consecutive days beginning 5 hours after inoculation. The animals were assessed daily for deaths. The results are displayed in FIG. 2 which charts the survival rate against time. In the legend, the compound of the invention is denoted Ex.29 and acyclovir is denoted ACV. The percentage of mice surviving the HSV-1 infection was significantly greater following a given dose of the compound of the invention relative to an equivalent dose of acyclovir.

The foregoing is merely illustrative of the invention and is not intended to limit the invention to the disclosures made herein. Variations and changes which are obvious to one skilled in the art are intended to be within the scope and nature of the invention as defined in the appended claims

The invention claimed is:

1. A method for the treatment of a viral infection caused by a herpes virus comprising administering an effective amount of a compound having Formula I

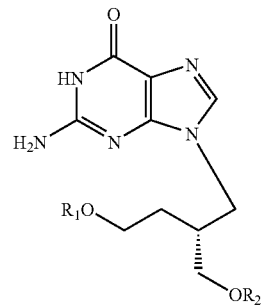

where a) $R_1$ is —C(O)CH(CH(CH$_3$)$_2$)NH$_2$ or —C(O)CH(CH(CH$_3$)CH$_2$CH$_3$)NH$_2$ and $R_2$ is —C(O)C$_3$-C$_{21}$ saturated or monounsaturated substituted alkyl, optionally substituted with up to five similar or different substituents independently selected from the group consisting of hydroxy, C$_1$-C$_6$ alkyl, C$_1$-C$_6$ alkoxy, C$_1$-C$_6$ alkoxy C$_1$-C$_6$ alkyl, C$_1$-C$_6$ alkanoyl, amino, halo, cyano, azido, oxo, mercapto and nitro; or b) $R_1$ is —C(O)C$_3$-C$_{21}$ saturated or monounsaturated alkyl, optionally substituted with up to five similar or different substituents independently selected from the group consisting of hydroxy, C$_1$-C$_6$ alkyl, C$_1$-C$_6$ alkoxy, C$_1$-C$_6$ alkoxy C$_1$-C$_6$ alkyl, C$_1$-C$_6$ alkanoyl, amino, halo, cyano, azido, oxo, mercapto and nitro, and $R_2$ is —C(O)CH(CH(CH$_3$)$_2$)NH$_2$ or —C(O)CH(CH(CH$_3$)CH$_2$CH$_3$)NH$_2$;

or a pharmaceutically acceptable salt thereof to a human or animal in need thereof.

2. A method according to claim 1, wherein $R_1$ is —C(O)CH(CH(CH$_3$)$_2$)NH$_2$ or —C(O)CH(CH(CH$_3$)CH$_2$CH$_3$)NH$_2$ and $R_2$ is —C(O)C$_3$-C$_{21}$ saturated or monounsaturated alkyl optionally substituted with up to five similar or different substituents independently selected from the group consisting of hydroxy, C$_1$-C$_6$ alkyl, C$_1$-C$_6$ alkoxy, C$_1$-C$_6$ alkoxy C$_1$-C$_6$ alkyl, C$_1$-C$_6$ alkanoyl, amino, halo, cyano, azido, oxo, mercapto and nitro.

3. A method according to claim 1 wherein $R_1$ or $R_2$ is a —C(=O) C$_9$ to C$_{17}$, saturated or N:9 monounsaturated, alkyl.

4. A method according to claim 1, wherein the compound is selected from the group consisting of:
(R)-9-[2-(Stearoyloxymethyl)-4-(L-valyloxy)butyl]guanine,
(R)-9-[2-(Myristoyloxymethyl)-4-(L-valyloxy)butyl]guanine,
(R)-9-[2-(Oleoyloxymethyl)-4-(L-valyloxy)butyl]guanine,
(R)-9-[2-(Butyrloxymethyl)-4-(L-valyloxy)butyl]guanine,
(R)-9-[2-(Decanoyloxymethyl)-4-(L-valyloxy)butyl]guanine,
(R)-9-[2-(Docosanoyloxymethyl)-4-(L-valyloxy)butyl]guanine,
(R)-9-[4-(L-Isoleucyloxy)-2-(stearoyloxyrnethyl)butyl]guanine,
(R)-9-[2-(Decanoyloxymethyl)-4-(L-isoleucyloxy)butyl]guanine,
(R)-9-[4-(L-Isoleucyloxy)-2-(myristoyloxymethyl)butyl]guanine,
(R)-9-[2-(4-Acetylbutyryloxymethyl-4-(L-valyloxy)butyl]guanine,
(R)-9-[2-Dodecanoyloxymethyl-4-(L-valyloxy)butyl]guanine, (R)-9-[2-Palmitoyloxymethyl-4-(L-valyloxy)butyl]guanine, (R)-9-[2-(L-Valyloxymethyl)-4-(stearoyloxy) butyl]guanine or a pharmaceutically acceptable salt thereof.

5. A method according to claim 1, wherein the compound is denoted (R)-9-[2-(Stearoyloxymethyl)-4-(L-valyloxy)butyl]guanine or a pharmaceutically acceptable salt thereof.

6. The method according to claim 1, wherein said herpes virus is selected from the group consisting of Type 1 Herpes simplex, Type II Herpes simplex, *Varicella zoster* virus, Epstein Barr virus, Herpes type 6 and HHV-8.

7. The method according to claim 5, wherein said herpes virus is selected from the group consisting of Type 1 Herpes simplex, Type II Herpes simplex, *Varicella zoster* virus, Epstein Barr virus, Herpes type 6 and HHV-8.

* * * * *